(12) United States Patent
Burkett

(10) Patent No.: US 9,943,235 B2
(45) Date of Patent: *Apr. 17, 2018

(54) SIDE-LOADING CONNECTORS FOR USE WITH INTRAVASCULAR DEVICES AND ASSOCIATED SYSTEMS AND METHODS

(71) Applicant: Volcano Corporation, San Diego, CA (US)

(72) Inventor: David H. Burkett, Temecula, CA (US)

(73) Assignee: VOLCANO CORPORATION, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/418,415

(22) Filed: Jan. 27, 2017

(65) Prior Publication Data
US 2017/0135588 A1    May 18, 2017

Related U.S. Application Data

(63) Continuation of application No. 15/250,549, filed on Aug. 29, 2016, now Pat. No. 9,554,710, which is a (Continued)

(51) Int. Cl.
*H01R 24/00* (2011.01)
*A61B 5/0215* (2006.01)
(Continued)

(52) U.S. Cl.
CPC ........ *A61B 5/02055* (2013.01); *A61B 5/0035* (2013.01); *A61B 5/0066* (2013.01);
(Continued)

(58) Field of Classification Search
CPC . Y10S 439/909; H01R 24/58; H01R 2201/12; H01R 13/353; A61N 1/08; A61N 1/056; A61B 5/02055; A61B 5/0035
See application file for complete search history.

(56) References Cited

U.S. PATENT DOCUMENTS 4,675,007 A   6/1987  Terry
5,843,141 A  12/1998  Bischoff
(Continued)

FOREIGN PATENT DOCUMENTS

WO    2004041347    5/2004

*Primary Examiner* — Xuong Chung Trans

(57) ABSTRACT

Intravascular devices, systems, and methods are disclosed. In some embodiments, side-loading electrical connectors for use with intravascular devices are provided. The side-loading electrical connector has at least one electrical contact configured to interface with an electrical connector of the intravascular device. A first connection piece of the side-loading electrical connector is movable relative to a second connection piece between an open position and a closed position, wherein in the open position an elongated opening is formed between the first and second connection pieces to facilitate insertion of the electrical connector between the first and second connection pieces in a direction transverse to a longitudinal axis of the intravascular device and wherein in the closed position the at least one electrical contact is electrically coupled to the at least one electrical connector received between the first and second connection pieces.

9 Claims, 22 Drawing Sheets

Related U.S. Application Data continuation of application No. 13/930,636, filed on Jun. 28, 2013, now Pat. No. 9,427,163.

(60) Provisional application No. 61/665,748, filed on Jun. 28, 2012.

(51) Int. Cl.

| | | |
|---|---|---|
| *A61B 5/0205* | (2006.01) | |
| *A61B 8/12* | (2006.01) | |
| *A61B 5/00* | (2006.01) | |
| *H01R 13/453* | (2006.01) | |
| *H01R 13/631* | (2006.01) | |
| *H01R 13/717* | (2006.01) | |

(52) U.S. Cl.
CPC ........ *A61B 5/0215* (2013.01); *A61B 5/02158* (2013.01); *A61B 8/12* (2013.01); *H01R 13/453* (2013.01); *H01R 13/631* (2013.01); *H01R 13/717* (2013.01); *A61B 2562/227* (2013.01); *A61B 2562/228* (2013.01); *H01R 2201/12* (2013.01)

(56) References Cited

U.S. PATENT DOCUMENTS

| | | | |
|---|---|---|---|
| 5,931,861 A | 8/1999 | Werner | |
| 6,174,809 B1 | 1/2001 | Kang | |
| 6,321,126 B1 | 11/2001 | Kuzm | |
| 6,605,049 B1 * | 8/2003 | Wagner | A61M 25/09 600/585 |
| 6,896,541 B2 * | 5/2005 | Benson | H01R 13/641 439/188 |
| 7,130,699 B2 | 10/2006 | Huff | |
| 7,261,580 B1 | 8/2007 | Secira | |
| 7,314,392 B2 * | 1/2008 | Pharn | H01R 13/641 439/489 |
| 7,914,319 B2 * | 3/2011 | Jones | H01R 13/641 439/489 |
| 8,007,440 B2 | 8/2011 | Magnin | |
| 8,162,684 B1 | 4/2012 | Sochor | |
| 8,932,208 B2 | 1/2015 | Kendale | |
| 9,427,163 B2 * | 8/2016 | Burkett | A61B 5/0215 |
| 9,554,710 B2 * | 1/2017 | Burkett | A61B 5/0215 |
| 2005/0187535 A1 | 8/2005 | Wilson | |
| 2010/0063383 A1 | 3/2010 | Anderson | |

* cited by examiner

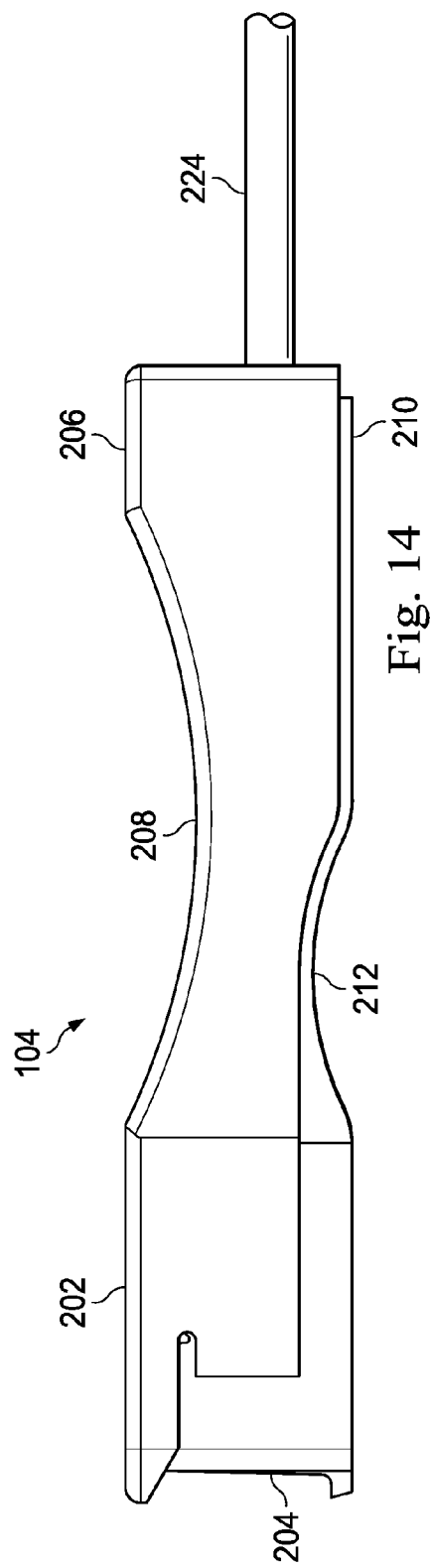
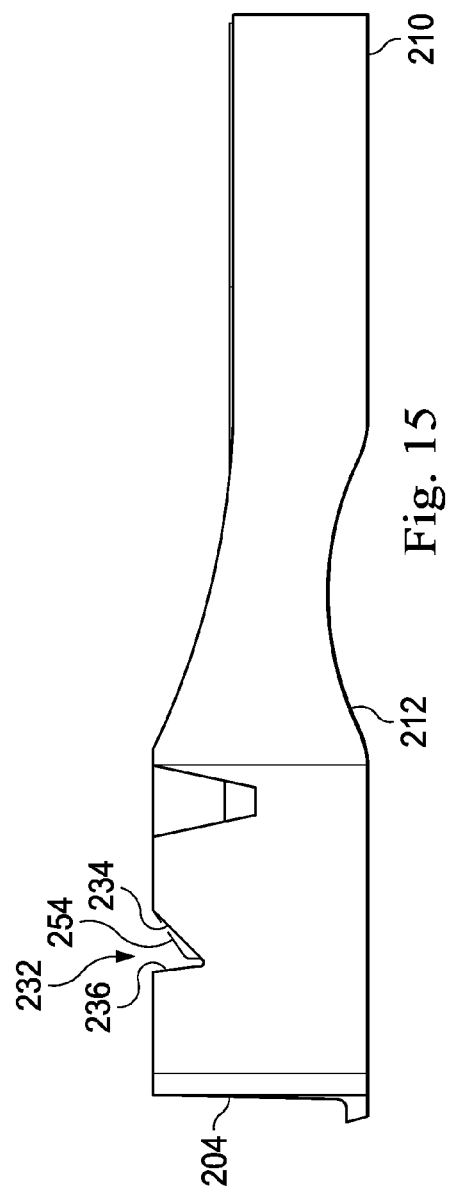

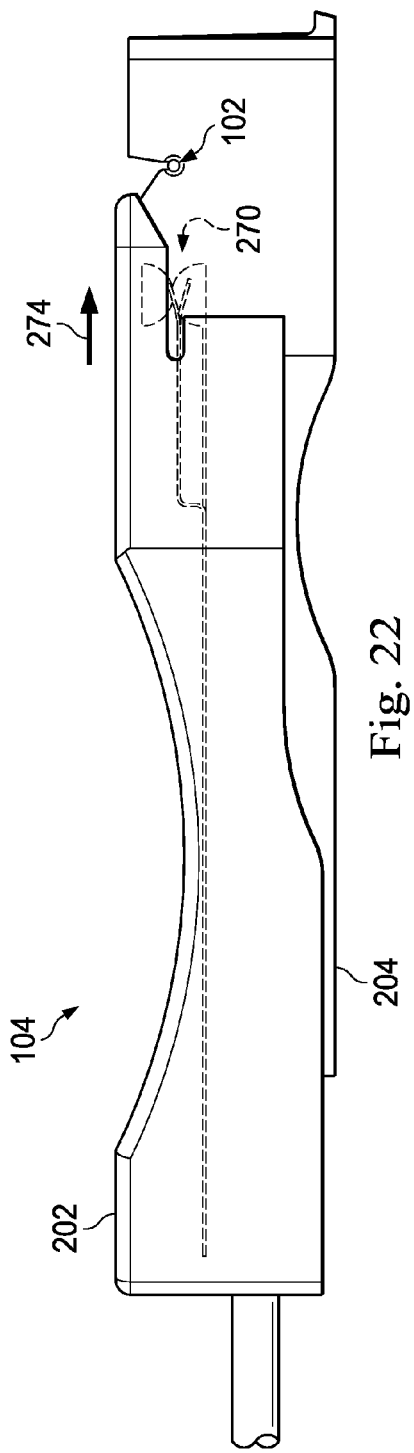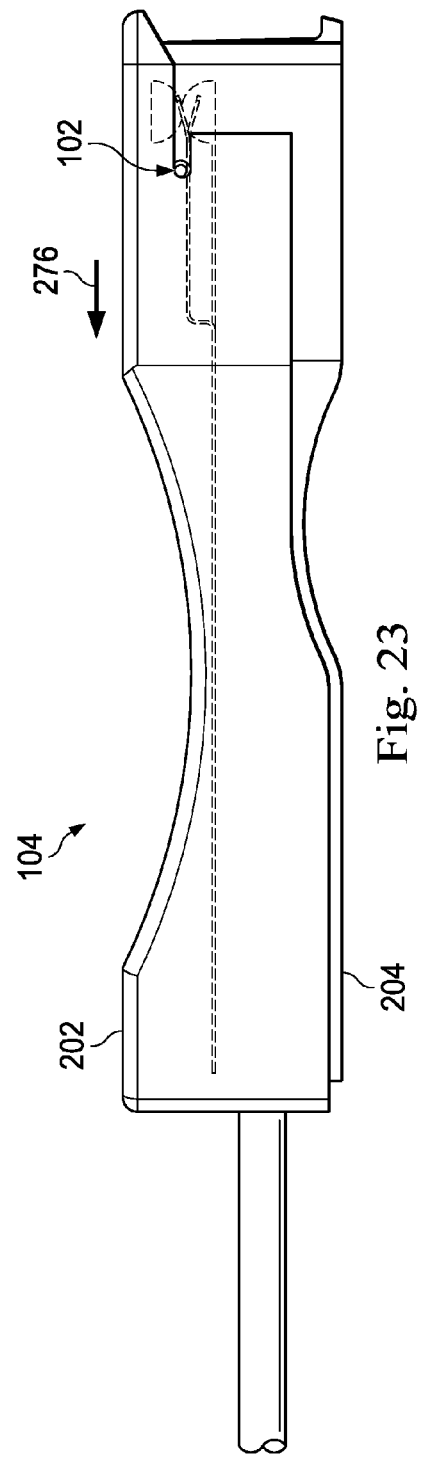

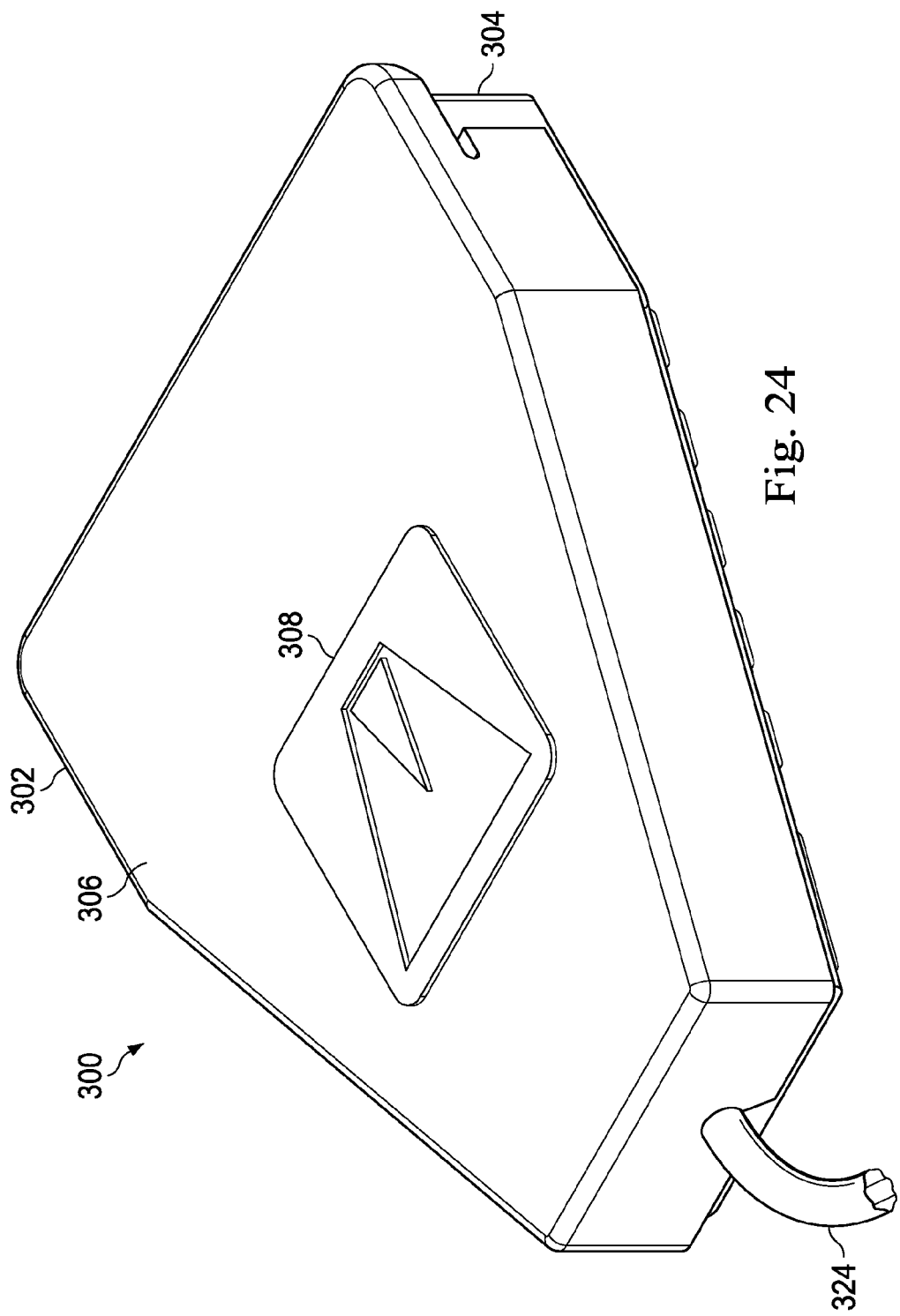

SIDE-LOADING CONNECTORS FOR USE WITH INTRAVASCULAR DEVICES AND ASSOCIATED SYSTEMS AND METHODS

CROSS REFERENCE TO RELATED APPLICATIONS

The present application is a continuation of U.S. Non-Provisional patent application Ser. No. 15/250,549, filed Aug. 29, 2016, now U.S. Pat. No. 9,554,710, which is a continuation of U.S. Non-Provisional patent application Ser. No. 13/930,636, filed Jun. 28, 2013, now U.S. Pat. No. 9,427,163, which claims priority to and the benefit of U.S. Provisional Patent Application No. 61/665,748, filed Jun. 28, 2012, each of which is hereby incorporated by reference herein in its entirety.

TECHNICAL FIELD

The present disclosure relates to intravascular devices, systems, and methods. In some embodiments, the intravascular devices are guidewires that include one or more electronic components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guidewires are utilized to measure the pressure within the blood vessel. To date, guidewires containing pressure sensors or other electronic components have suffered from reduced performance characteristics compared to standard guidewires that do not contain electronic components. For example, the handling performance of previous guidewires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guidewire. Further, due to its small diameter, in many instances the proximal connector portion of the guidewire (i.e., the connector(s) that facilitate communication between the electronic component(s) of the guidewire and an associated controller or processor) is fragile and prone to kinking, which destroys the functionality of the guidewire. For this reason, surgeons are reluctant to remove the proximal connector from the guidewire during a procedure for fear of breaking the guidewire when reattaching the proximal connector. However, having the guidewire coupled to the proximal connector further limits the maneuverability and handling of the guidewire.

Accordingly, there remains a need for improved connectors for use with intravascular devices (e.g., catheters and guidewires) that include one or more electronic components.

SUMMARY

Embodiments of the present disclosure are directed to intravascular devices, systems, and methods.

In one embodiment, an intravascular system is provided. The system includes an intravascular device comprising a flexible elongate member having a proximal portion and a distal portion, at least one electronic component secured to the distal portion of the flexible elongate member, and at least one electrical connector secured to the proximal portion of the flexible elongate member, wherein the at least one electrical connector is electrically coupled to the at least one electronic component secured to the distal portion of the flexible elongate member, wherein the at least one electrical connector has a first diameter and a section of the proximal portion of the flexible elongate member adjacent the at least one electrical connector has a second diameter less than the first diameter. The system also includes a connector having at least one electrical contact configured to interface with the at least one electrical connector of the intravascular device, the connector including a first connection piece and a second connection piece. The first connection piece is translatable relative to the second connection piece between an open position and a closed position. In the open position, the second connection piece is configured to receive the at least one electrical connector of the intravascular device in a direction transverse to a longitudinal axis of the intravascular device such that an alignment feature of the second connection piece engages the section of the proximal portion of the flexible elongate member adjacent the at least one electrical connector to align the at least one electrical connector of the intravascular device with the at least one electrical contact of the connector. In the closed position, the at least one electrical contact is electrically coupled to the at least one electrical connector.

In some embodiments, the connector includes a bias element, such as a spring, that urges the first and second connection pieces towards the closed position. In some instances, the second connection piece includes a recess sized and shaped to receive a portion of the intravascular device that includes the at least one electrical connector. The at least one electrical contact is secured to the first connection piece such that the at least one electrical contact is spaced from the recess of the second connection piece in the open position and extends across the recess of the second connection piece in the closed position in some implementations. In some instances, the at least one electrical connector consists of three electrical connectors. In some embodiments, the at least one electronic component includes at least one of a pressure sensing component, an intravascular imaging component, an ultrasound transducer, and an optical coherence tomography (OCT) imaging element. In some embodiments, the second connection piece includes at least one opening and the first connection piece includes at least one projection for movably engaging the at least one opening of the second connection piece such that the at least one opening guides translation of the first connection piece relative to the second connection piece. The at least one electrical contact comprises a split open comb electrical contact in some instances. In some embodiments, the connector comprises at least two electrical contacts and includes at least one element positioned between the at least two electrical contacts that is configured to remove fluid from a surface of the intravascular device when the first connection piece is moved between the open position and the closed position. In some implementations, the at least one element for removing fluid is a sponge. In some instances, the surface of the intravascular device that fluid is removed from is a surface of a non-conductive material positioned between two electrical connectors.

In another embodiment, a method is provided. The method includes providing a connector having a first component, a second component, and at least one electrical contact; moving the connector to an open position such an elongated opening of the second component of the connector is exposed; inserting a connection portion of an intravascular device into the elongated opening in a direction transverse to a longitudinal axis of the intravascular device such that an alignment feature of the second connection piece engages a proximal portion of the flexible elongate member to align the connection portion of the intravascular device with the at least one electrical contact of the connector; and moving the connector to a closed position to electrically couple the at least one electrical contact of the connector to at least one electrical connector of the connection portion of the intravascular device. In some instances, the at least one electrical connector is electrically connected to an electronic component positioned at a distal portion of the intravascular device such that the at least one electrical contact is electrically coupled to the electronic component when the at least one electrical contact is electrically coupled to the at least one electrical connector of the connection portion of the intravascular device.

In another embodiment, a connector for an intravascular system is provided. The connector includes a first connection piece having at least one electrical contact secured thereto; a second connection piece coupled to the first connection piece, wherein the first connection piece is translatable relative to the second connection piece between an open position and a closed position. In the open position, the second connection piece is configured to receive at least one electrical connector of an intravascular device in a direction transverse to a longitudinal axis of the intravascular device such that an alignment feature of the second connection piece engages a proximal portion of the flexible elongate member adjacent the at least one electrical connector to align the at least one electrical connector of the intravascular device with the at least one electrical contact of the first connection piece. In the closed position, the at least one electrical contact is electrically coupled to the at least one electrical connector.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 14 is a diagrammatic side view of the connector of FIGS. 5-13.

FIG. 15 is a diagrammatic side view of the connector similar to that of FIG. 14, but illustrating only a lower portion of the connector.

FIG. 22 is a diagrammatic side view of the connector of FIGS. 5-21 shown in an open position and receiving an intravascular device according to an embodiment of the present disclosure.

FIG. 23 is a diagrammatic side view of the connector of FIGS. 5-22 shown in a closed position and receiving an intravascular device according to an embodiment of the present disclosure.

FIG. 24 is a diagrammatic perspective rear view of a connector according to another embodiment of the present disclosure.

DETAILED DESCRIPTION

Figure 1:
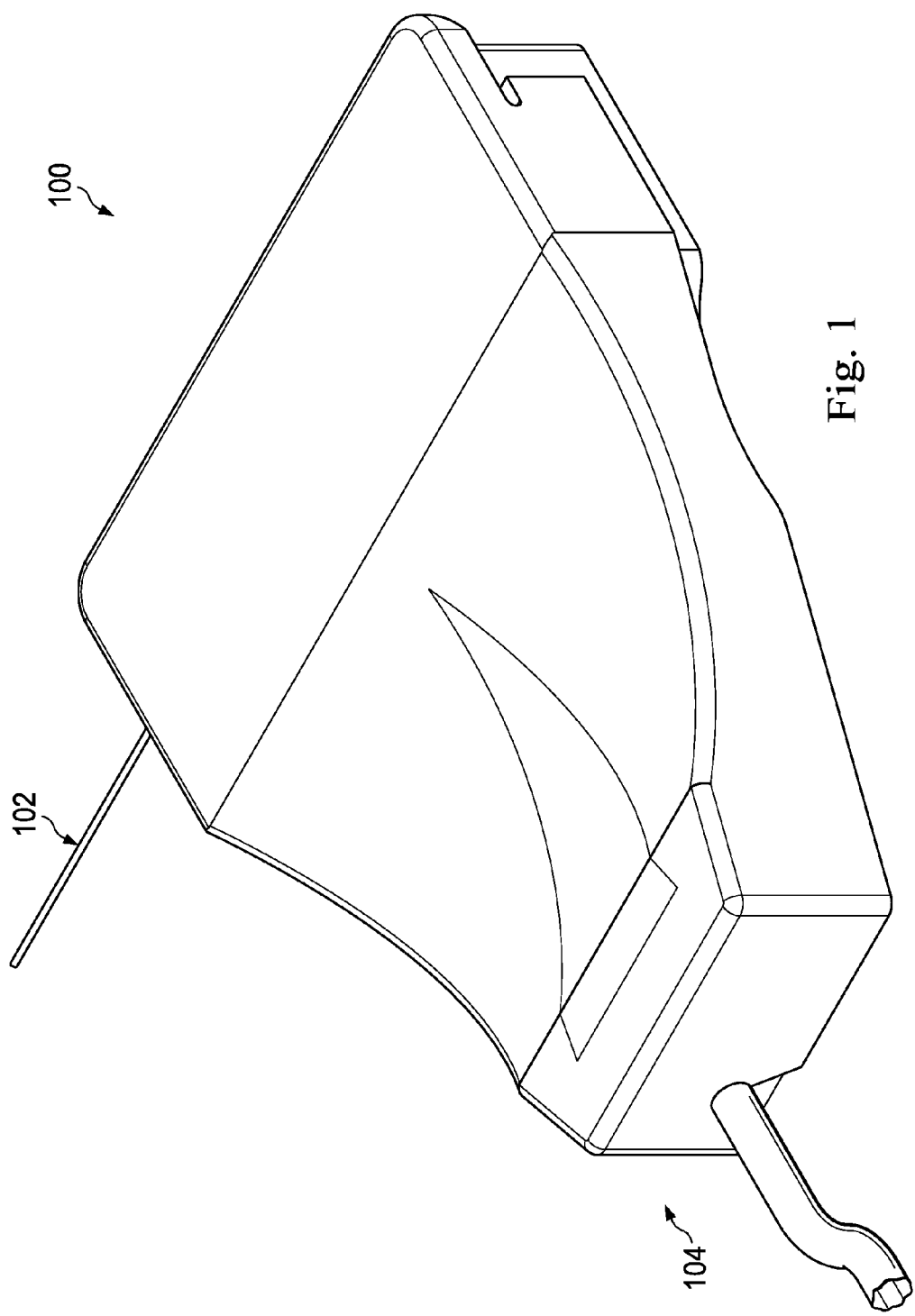
FIG. 1 is a diagrammatic perspective view of an intravascular system according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, intravascular catheters and intravascular guidewires. In that regard, intravascular catheters may or may not include a lumen extending along its length for receiving and/or guiding other instruments. If the intravascular catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an fro electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized. Further, in some instances the flexible elongate member includes multiple electronic, optical, and/or electro-optical components (e.g., pressure sensors, temperature sensors, imaging elements, optical fibers, ultrasound transducers, reflectors, mirrors, prisms, ablation elements, fro electrodes, conductors, etc.).

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guidewire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Figure 2:
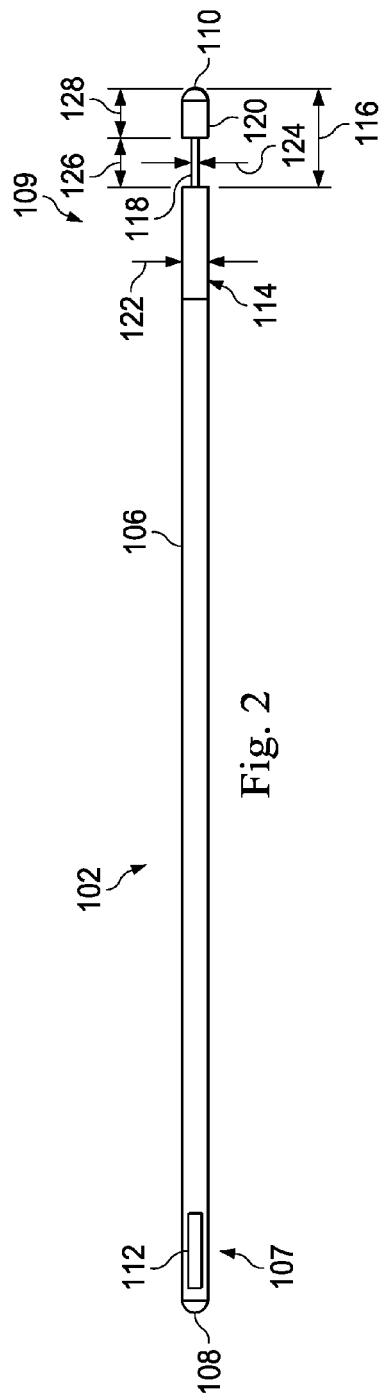
FIG. 2 is a diagrammatic side view of an intravascular device of the intravascular system of FIG. 1 according to an embodiment of the present disclosure.

Referring now to FIG. 1, shown therein is an intravascular system 100 according to an embodiment of the present disclosure. In that regard, the intravascular system includes an intravascular device 102 and a connector 104. Referring now to FIG. 2, a side view of the intravascular device 102 is provided according to an embodiment of the present disclosure. As shown, the intravascular device 102 includes a flexible elongate member 106 having a distal portion 107 adjacent a distal end 108 and a proximal portion 109 adjacent a proximal end 110. A component 112 is positioned within the distal portion 107 of the flexible elongate member 106 proximal of the distal tip 108. Generally, the component 112 is representative of one or more electronic, optical, or electro-optical components. In that regard, the component 112 is a pressure sensor, a temperature sensor, an imaging element, an optical fiber, an ultrasound transducer, a reflector, a mirror, a prism, an ablation element, an fro electrode, a conductor, and/or combinations thereof. The specific type of component or combination of components can be selected based on an intended use of the intravascular device. In some instances, the component 112 is positioned less than 10 cm, less than 5, or less than 3 cm from the distal tip 108. In some instances, the component 112 is positioned within a housing of the intravascular device 102. In that regard, the housing is a separate component secured to the flexible elongate member 106 in some instances. In other instances, the housing is integrally formed as a part of the flexible elongate member 106.

The intravascular device 102 also includes a connection portion 114 adjacent the proximal portion 109 of the device. In that regard, the connection portion 114 is spaced from the proximal end 110 of the flexible elongate member 106 by a distance 116. Generally, the distance 116 is between 0% and 50% of the total length of the flexible elongate member 106. While the total length of the flexible elongate member can be any length, in some embodiments the total length is between about 1300 mm and about 4000 mm, with some specific embodiments having a length of 1400 mm, 1900 mm, and 3000 mm. In some instances the connection portion 114 is spaced from the proximal end 110 between about 0 mm and about 1400 mm. In some specific embodiments, the connection portion 114 is spaced from the proximal end by a distance of 0 mm, 300 mm, and 1400 mm. Accordingly, in some instances the connection portion 114 is positioned at the proximal end 110. In some such embodiments, one or more aspects of the engagement and alignment features of the intravascular device 102 discussed below are positioned distal of the of the connection portion 114 instead of proximal of the connection portion 114 as shown in the embodiment of FIG. 2.

In that regard, in the illustrated embodiment of FIG. 2 the intravascular device 102 includes a section 118 extending proximally from the connection portion 114 to another section 120 that extends to proximal end 110. In the illustrated embodiment, the section 120 is rounded to proximal end 110. In other embodiments, the section 120 has a tapered, arcuate, and/or other changing profile as it extends proximally to proximal end 110. In that regard, in some instances the outer profile and/or diameter of the section 120 reduces as it extends proximally to proximal end 110 such that the reduced profile and/or diameter of the proximal end facilitates easier introduction of one or more other instruments over the intravascular device. In other embodiments, the section 120 has a constant profile as it extends proximally to proximal end 120.

As shown, the connection portion 114 has a diameter 122 (or other similar measurement for outer cross-section profiles for non-circular cross-sectional embodiments) while section 118 has a diameter 124 (again, or other similar measurement for outer cross-section profiles for non-circular cross-sectional embodiments). The diameter 124 of section 118 is different than the diameter 122 of connection portion 114. In that regard, the different sizes of the diameters 122, 124 create a structure that is configured to facilitate alignment and/or connection of the intravascular device 102 to a connector, such as connector 104. In the illustrated embodiment, the diameter 124 of section 118 is less than the diameter 122 of the connection portion 114. In some embodiments, the diameter 124 of section 118 is between about 40% and about 80% of diameter 122, with some particular embodiments being about 42%, 64%, and/or other percentage of diameter 122. In that regard, in some embodiments the diameter 122 of connection portion 114 is between about 0.0178 mm and about 3.0 mm, with some particular embodiments being 0.3556 mm (0.014") and 0.4572 mm (0.018"). Accordingly, in some embodiments the diameter 124 of section 118 is between about 0.007 mm and about 2.4 mm, with some particular embodiments being 0.15 mm, 0.19 mm, 0.23 mm, and 0.29 mm. In the illustrated embodiment, the section 120 has a diameter that is approximately equal to diameter 122 and, therefore, greater than diameter 124. However, in other embodiments, section 120 has a diameter that is greater than diameter 122, less than diameter 122, greater than diameter 124, equal to diameter 124, and/or less than diameter 124. In some embodiments, section 118 is a section of a core wire extending through the connection portion 114.

As shown in FIG. 2, the section 118 extends proximally from connection portion 114 a distance 126, while section 120 extends proximally from section 118 to proximal end 110 a distance 128. Together, distances 126 and 128 equal the distance 116 that the connection portion 114 is spaced from the proximal end 110 of the intravascular device 102. In some instances, the distance 126 of is between about 0.508 mm (0.020") and about 2.54 mm (0.10"), with some particular embodiments being 0.762 mm (0.030"), 1.016 mm (0.040"), and 1.524 mm (0.060"). Further, while the transition between connection portion 114 and section 118 and the transition between section 118 and section 120 are shown as being stepped in the illustrated embodiments, in other embodiments the transitions are tapered and/or otherwise make a gradual change in outer diameter along the length of the intravascular device. In some embodiments, use of tapered and/or gradual transitions results in the proximal portion of the intravascular device 102 not having any sharp edges. In some implementations, the use of tapered and/or gradual transitions for one or both of the transitions between section 118 and either the connection portion 114 or section 120 makes cleaning the proximal portion of the device (e.g., to remove any liquids or other unwanted materials on the surface of the proximal portion of the intravascular device) easier.

The connection portion 114 is configured to facilitate communication between the intravascular device 102 and another device. More specifically, in some embodiments the connection portion 114 is configured to facilitate communication of data obtained by the component 112 to another device, such as a computing device or processor. Accordingly, in some embodiments the connection portion 114 is an electrical connector. In such instances, the connection portion 114 is configured to provide an electrical connection to one or more electrical conductors that extend along the length of the flexible elongate member 102 and are electrically coupled to the component 112. In some instances, the connection portion 114 includes one or more electrical connectors as described in U.S. Patent Application No. 61/665,697, titled "INTRAVASCULAR DEVICES, SYSTEMS, AND METHODS," filed Jun. 28, 2012, which is hereby incorporated by reference in its entirety. In other embodiments, the connection portion 114 includes an optical connector. In such instances, the connection portion 114 provides an optical connection to one or more optical communication pathways (e.g., fiber optic cable) that extend along the length of the flexible elongate member 106 and are optically coupled to the component 112. Further, in some embodiments the connection portion 114 provides both electrical and optical connections to both electrical conductor(s) and optical communication pathway(s) coupled to the component 112. In that regard, it should again be noted that component 112 is comprised of a plurality of elements in some instances. In some instances, the connection portion 114 is configured to provide a physical connection to another device, either directly or indirectly. In other instances, the connection portion 114 is configured to facilitate wireless communication between the intravascular device 102 and another device. Generally, any current or future developed wireless protocol(s) may be utilized. In yet other instances, the connection portion 114 facilitates both physical and wireless connection to another device.

As noted above, in some instances the connection portion 114 provides a connection between the component 112 of the intravascular device 102, 120 and an external device. Accordingly, in some embodiments one or more electrical conductors, one or more optical pathways, and/or combinations thereof extend along the length of the flexible elongate member 106 between the connection portion 114 and the component 112 to facilitate communication between the connection portion 114 and the component 112. Generally, any number of electrical conductors, optical pathways, and/or combinations thereof can extend along the length of the flexible elongate member 106 between the connection portion 114 and the component 112. In some instances, between one and ten electrical conductors and/or optical pathways extend along the length of the flexible elongate member 106 between the connection portion 114 and the component 112. For the sake of clarity and simplicity, the embodiments of the present disclosure described below include three electrical conductors and, therefore, the connection portion 114 is described as having three separate electrical connections corresponding to the three electrical conductors.

Figure 3:
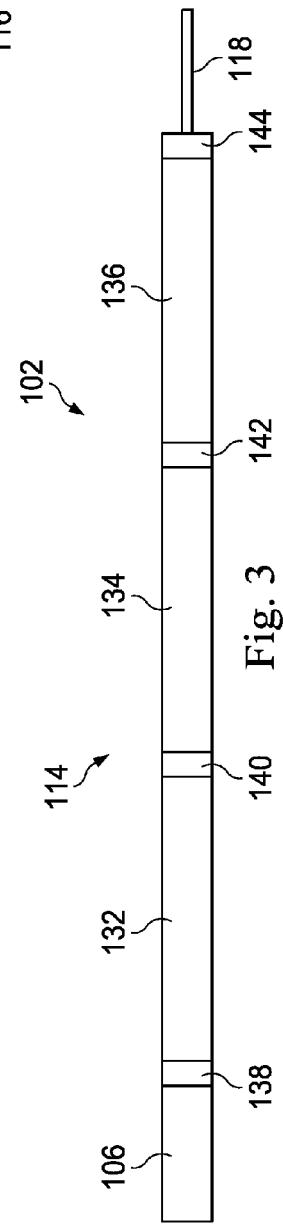
FIG. 3 is a diagrammatic side view of a proximal connector portion of an intravascular device according to an embodiment of the present disclosure.
Figure 4:
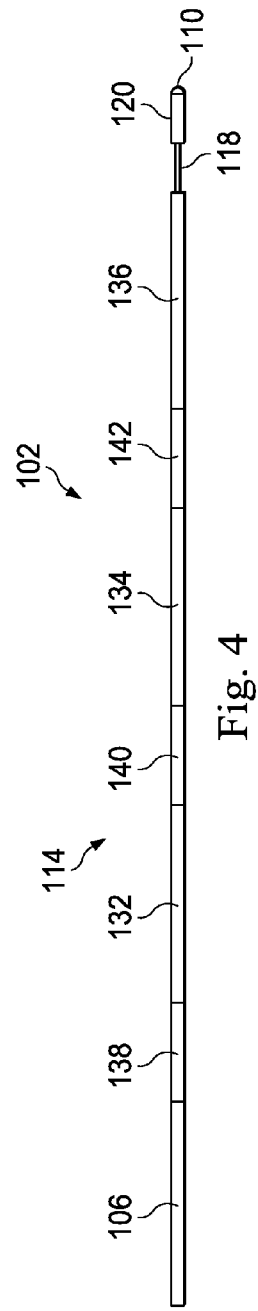
FIG. 4 is a diagrammatic side view of a proximal connector portion of an intravascular device similar to that of FIG. 3, but illustrating another embodiment of the present disclosure.

For example, as shown in FIG. 3, in some instances the connection portion 114 includes conductive portions 132, 134, and 136 that are separated from one another and the main body of the flexible elongate member 106 by insulating portions 138, 140, 142, and 144. In that regard, the conductive portions 132, 134, and 136 are formed of a conductive material and are portions of a hypotube, a coil, and/or combinations thereof in some instances. It is understood that the total number of communication pathways and/or the number of electrical conductors and/or optical pathways is different in other embodiments and, therefore, the number of conductive portions (or optical connectors) included in connection portion is different as well. More specifically, the number of communication pathways and the number of electrical conductors and optical pathways extending along the length of the flexible elongate member 106 is determined by the desired functionality of the component 112 and the corresponding elements that define component 112 to provide such functionality. As a result, the number and type of connections provided by connection portion 114 are likewise determined by the desired functionality of the component 112, the corresponding elements that define component 112 to provide such functionality, and the communication needs for such elements. Further still, in some instances, one or more of the insulating portions 138, 140, 142, and 144 is omitted. For example, as shown in the exemplary embodiment of FIG. 4, insulating portion 144 has been omitted.

Figure 5:
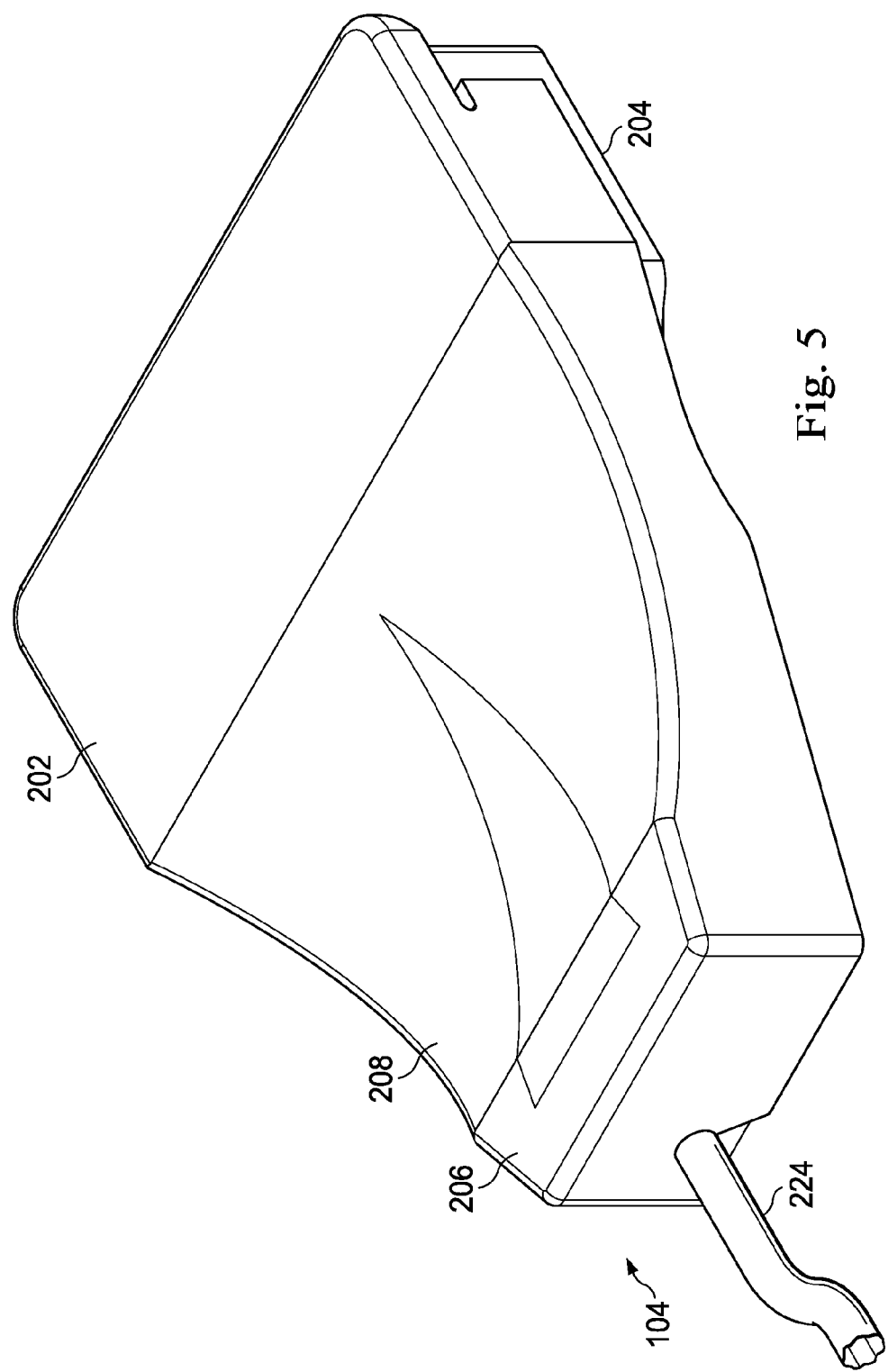
FIG. 5 is a diagrammatic perspective rear view of a connector of the intravascular system of FIG. 1 according to an embodiment of the present disclosure.
Figure 6:
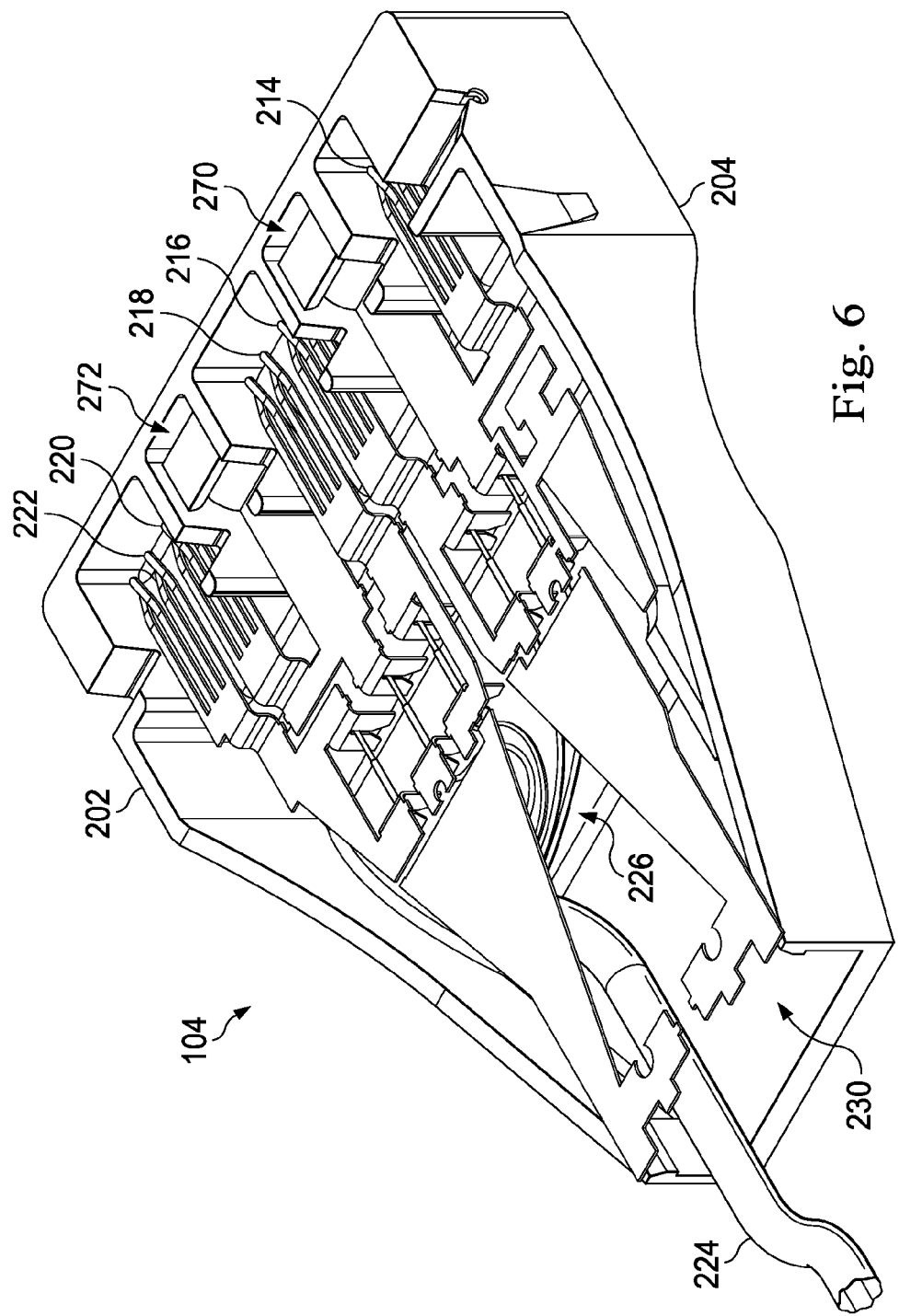
FIG. 6 is a diagrammatic perspective rear view of the connector similar to that of FIG. 5, but with portions of the connector removed to illustrate inner components of the connector.
Figure 7:
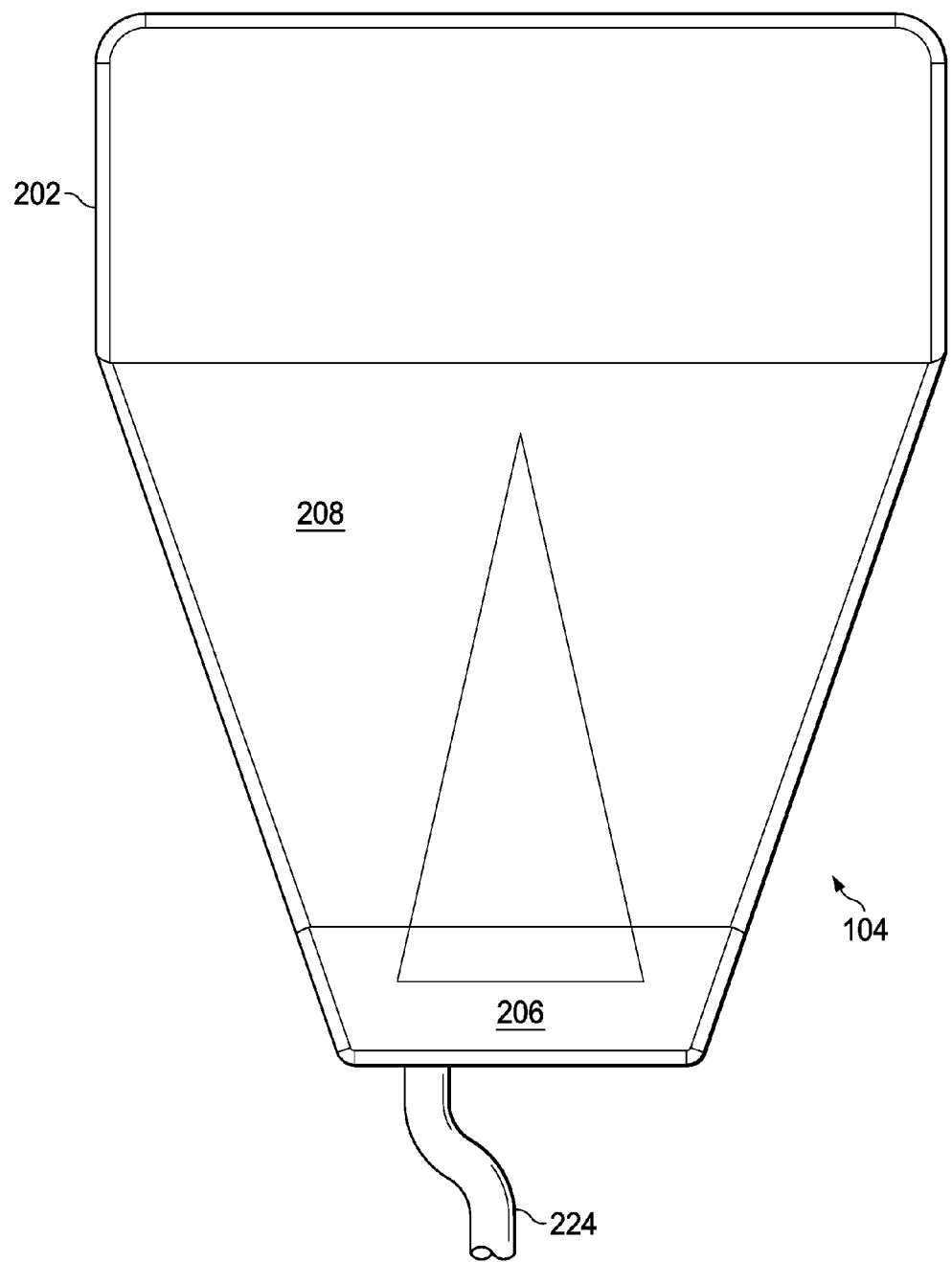
FIG. 7 is a diagrammatic top view of the connector of FIGS. 5 and 6.
Figure 8:
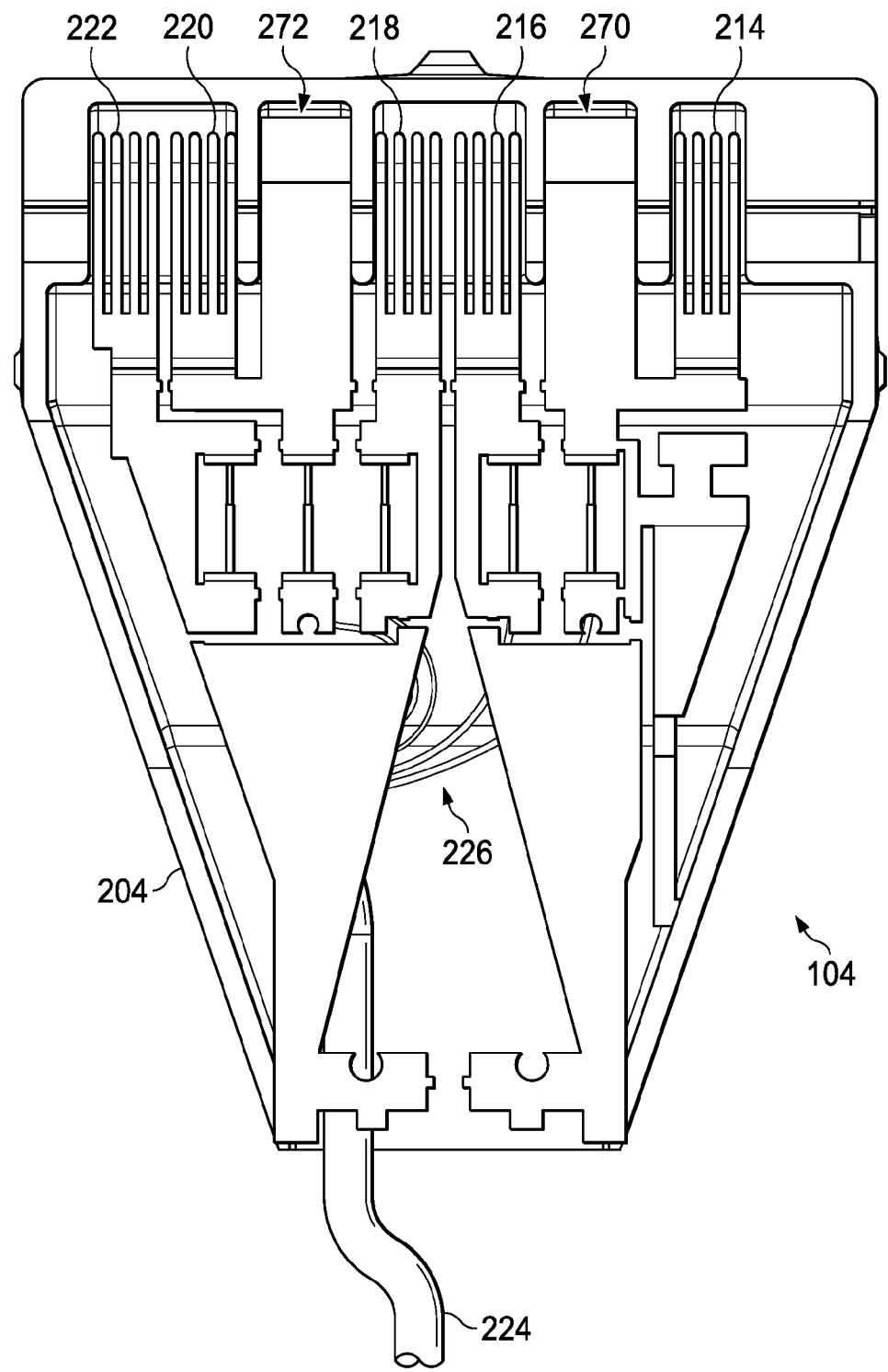
FIG. 8 is a diagrammatic top view of the connector similar to that of FIG. 7, but with portions of the connector removed to illustrate inner components of the connector.
Figure 9:
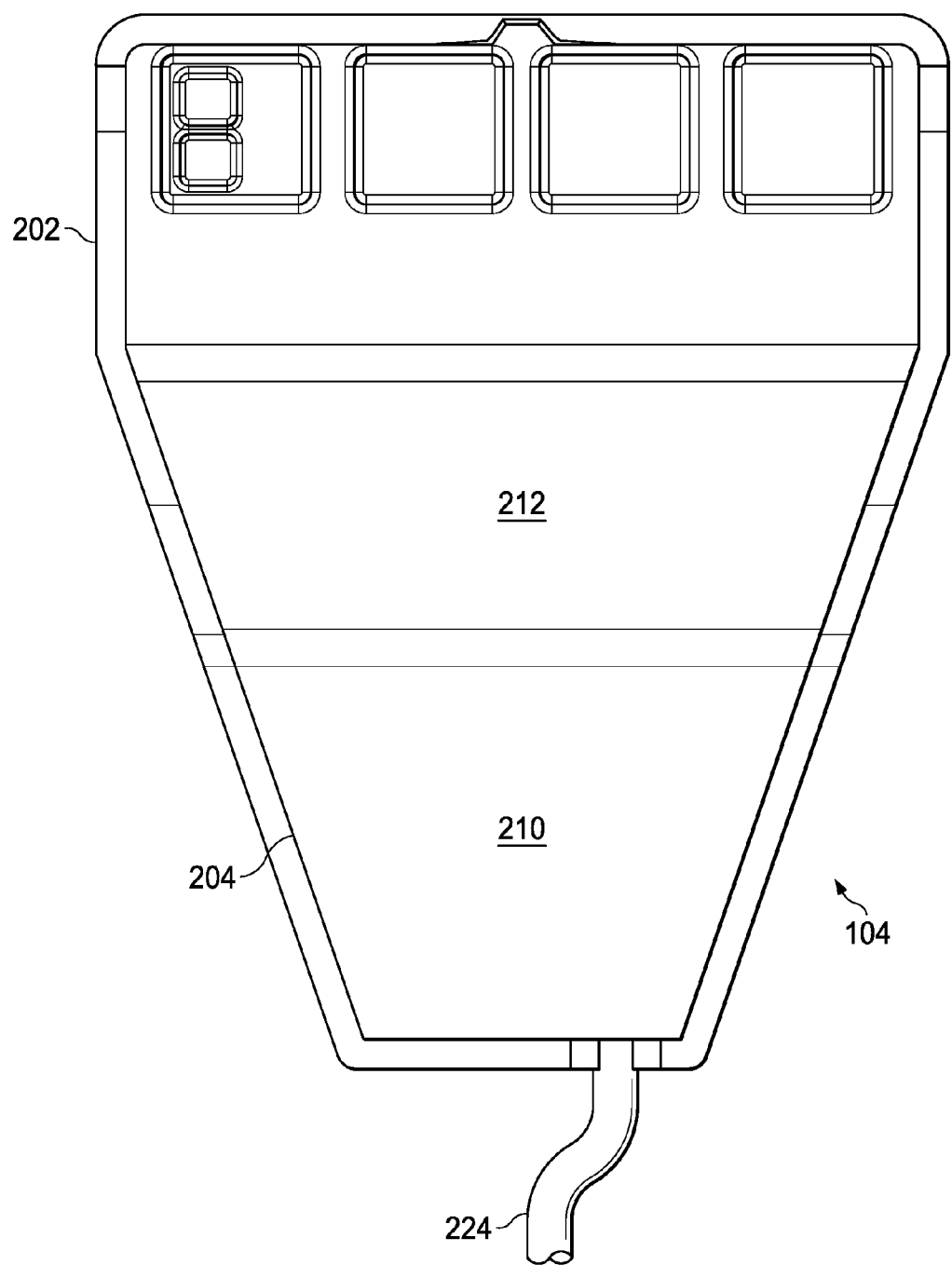
FIG. 9 is a diagrammatic bottom view of the connector of FIGS. 5-8.
Figure 10:
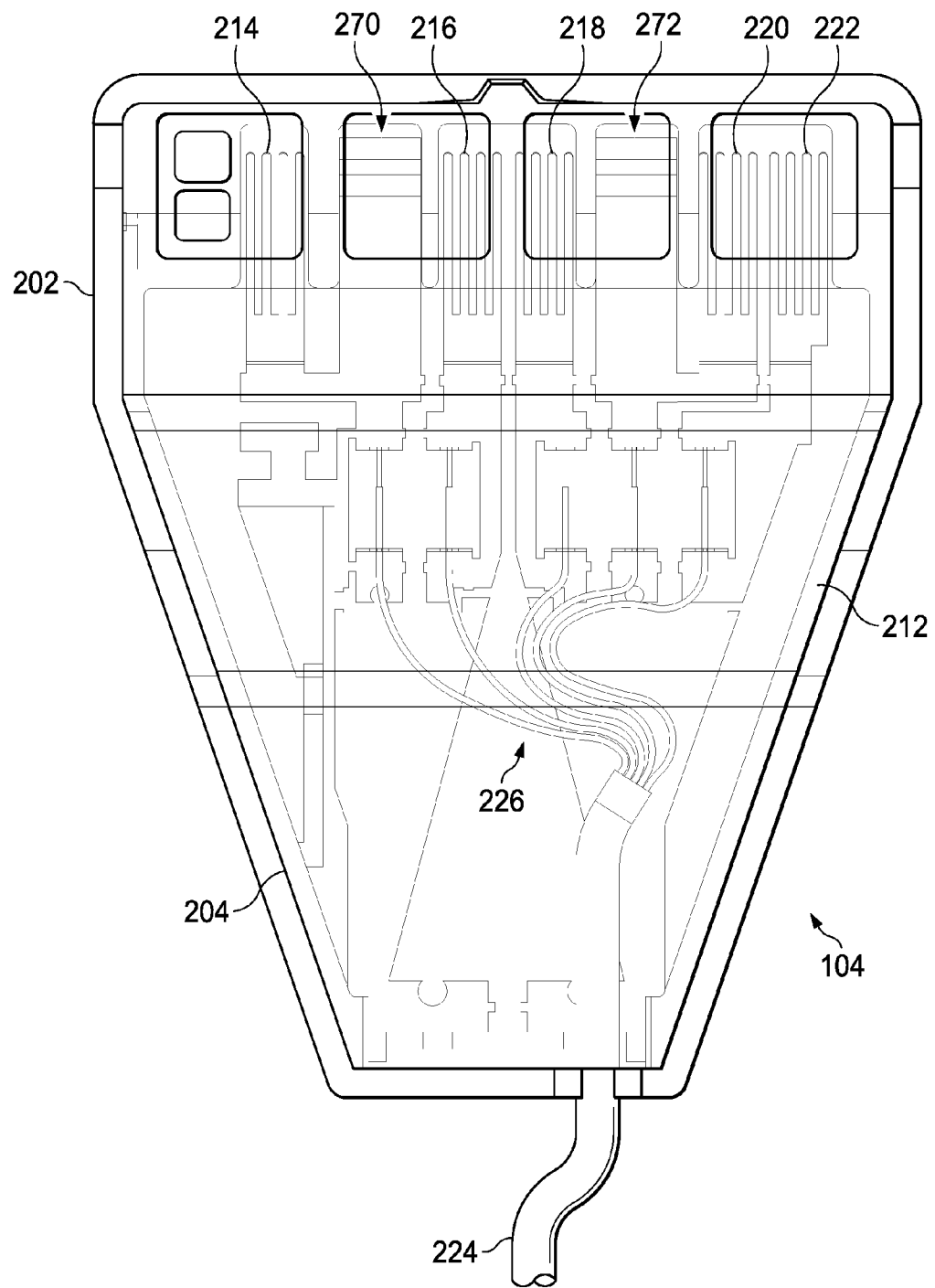
FIG. 10 is a diagrammatic bottom view of the connector similar to that of FIG. 9, but with the inner components of the connector illustrated.
Figure 11:
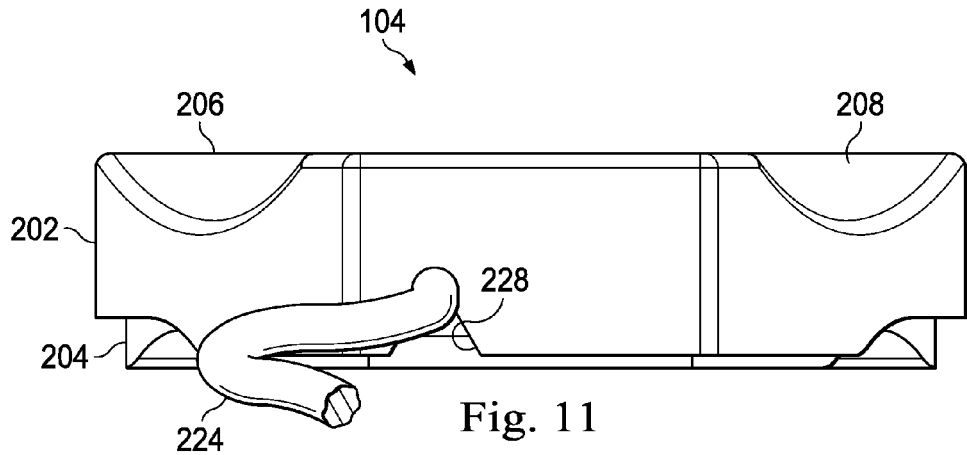
FIG. 11 is a diagrammatic rear view of the connector of FIGS. 5-10.
Figure 12:
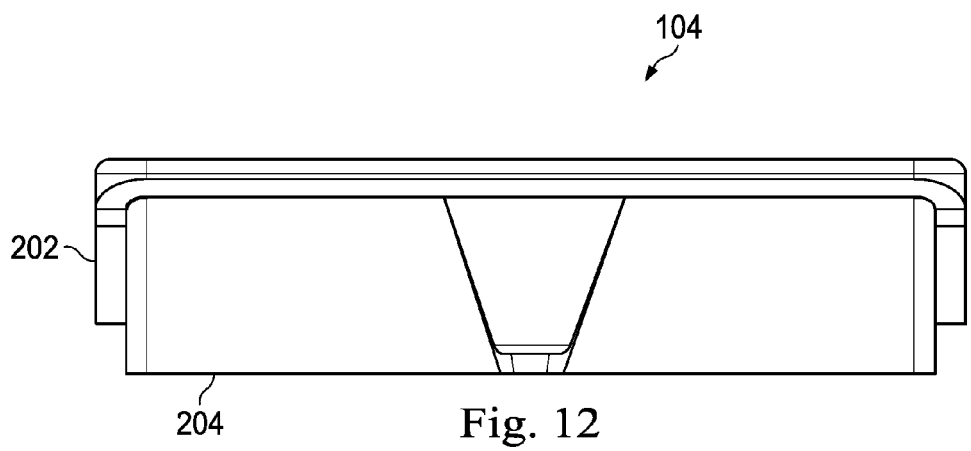
FIG. 12 is a diagrammatic front view of the connector of FIGS. 5-11.
Figure 13:
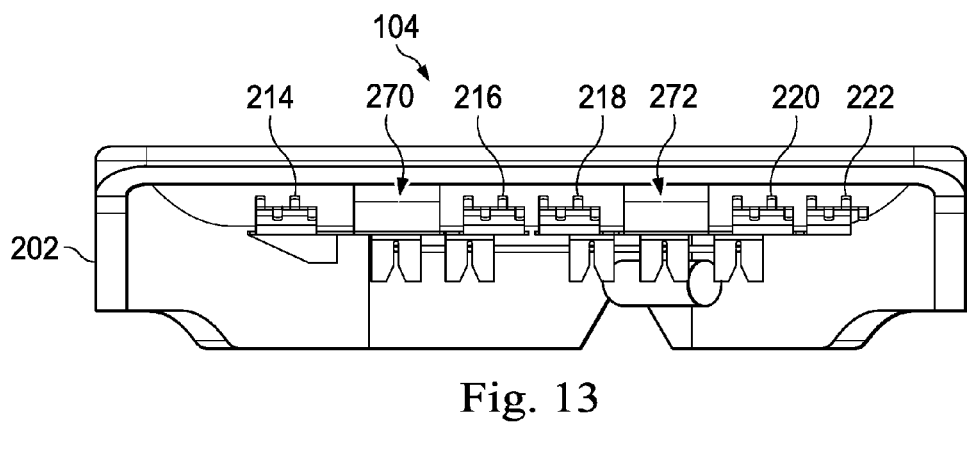
FIG. 13 is a diagrammatic front view of the connector similar to that of FIG. 13, but illustrating only an upper portion of the connector and inner components of the upper portion.
Figure 16:
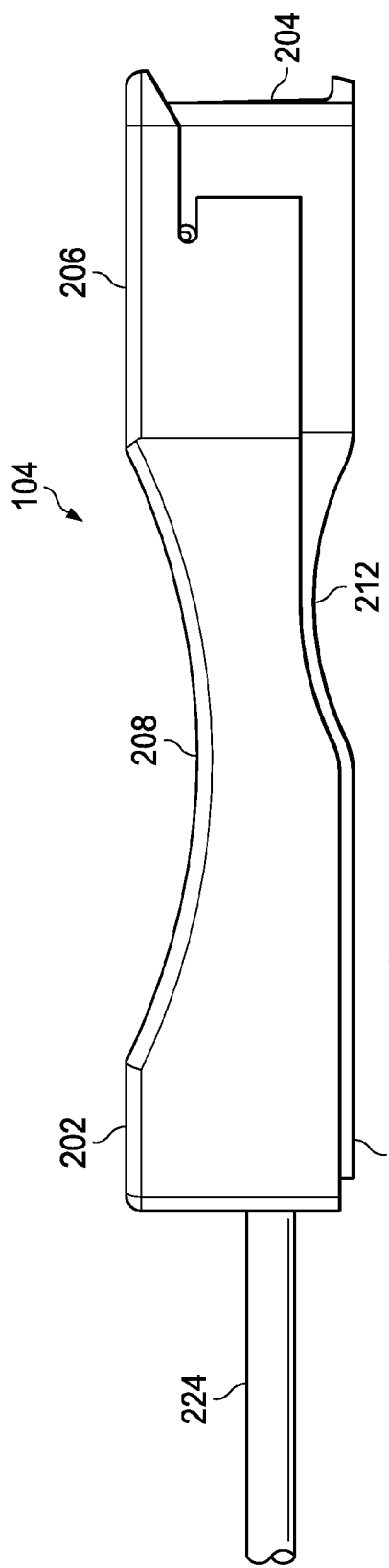
FIG. 16 is a diagrammatic side view of the connector of FIGS. 5-15 similar to that of FIG. 14, but from the opposite side of the connector.
Figure 17:
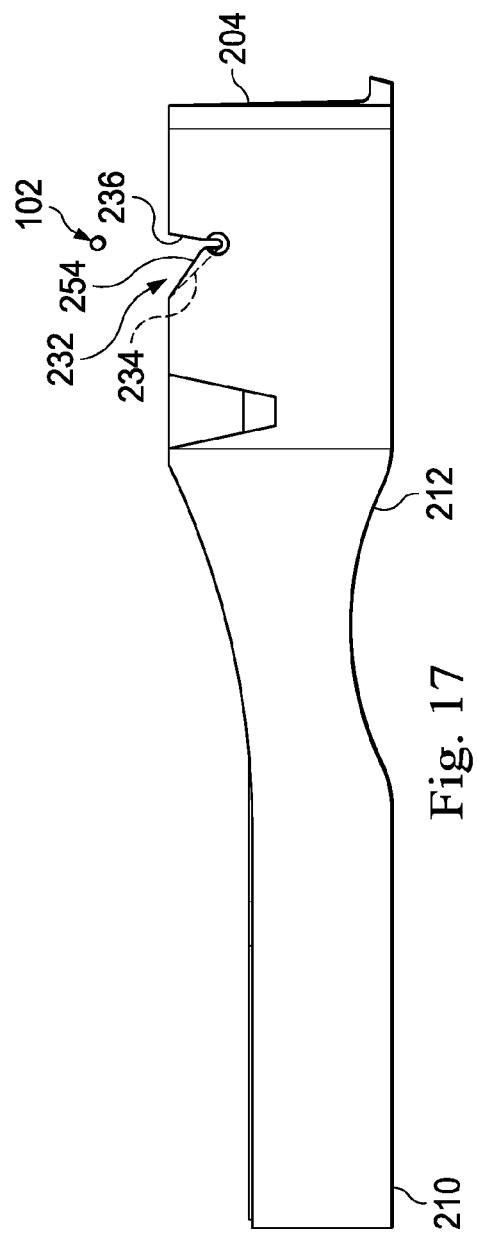
FIG. 17 is a diagrammatic side view of the connector similar to that of FIG. 15, but illustrating only a lower portion of the connector and showing the intravascular device positioned proximate to the lower portion of the connector.
Figure 18:
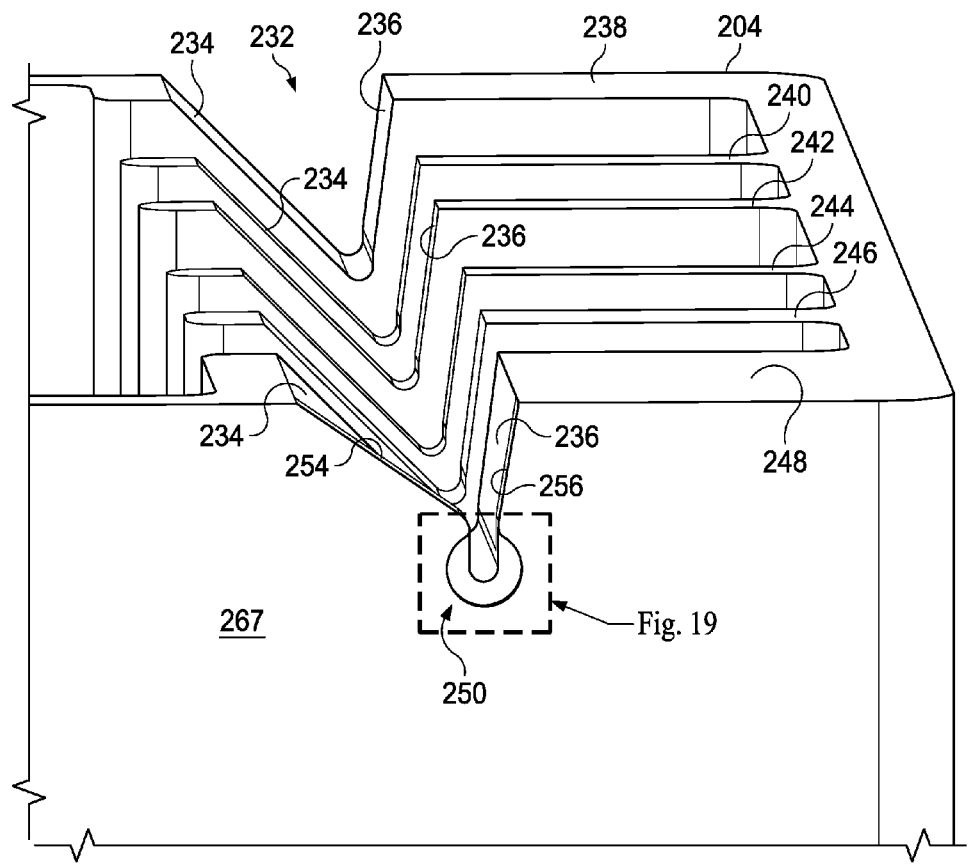
FIG. 18 is a close up diagrammatic side perspective view of a part of the lower portion of the connector of FIGS. 5-16.
Figure 19:
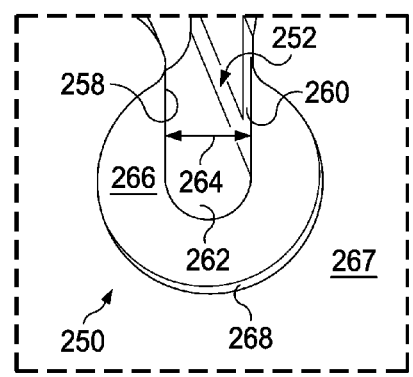
FIG. 19 is a close up diagrammatic side perspective view of an alignment feature of the part of the lower portion of the connector shown in FIG. 17.
Figure 20:
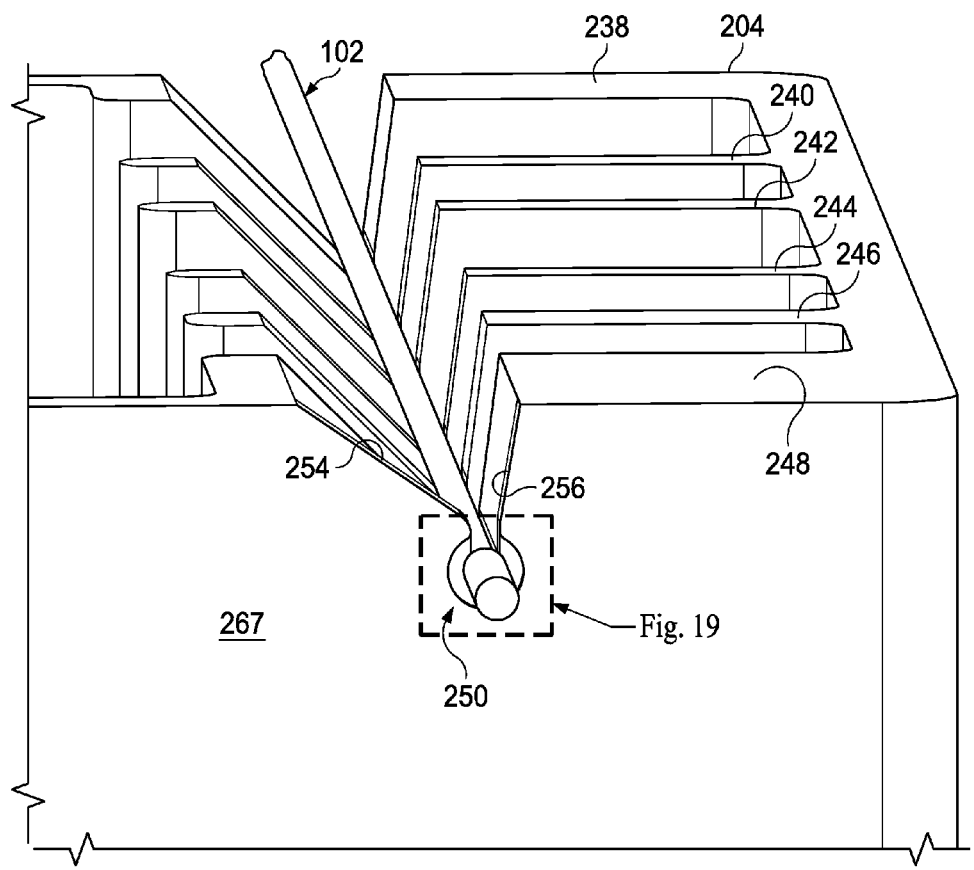
FIG. 20 is a close up diagrammatic side perspective view of a part of the lower portion of the connector similar to that of FIG. 17, but showing an intravascular device positioned within the lower portion.
Figure 21:
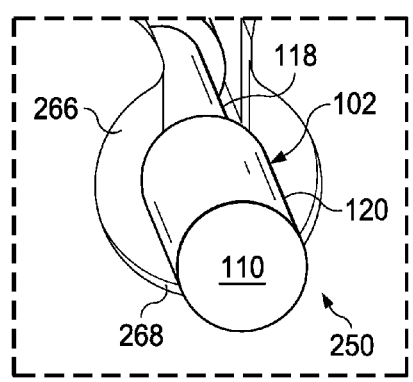
FIG. 21 is a close up diagrammatic side perspective view of the alignment feature of the part of the lower portion of the connector similar to that of FIG. 18, but showing an intravascular device positioned within the lower portion.

Referring now to FIGS. 5-24, shown therein are additional details of the connector 104. In that regard, FIG. 5 is a diagrammatic perspective rear view of the connector; FIG. 6 is a diagrammatic perspective rear view of the connector with portions of the connector removed to illustrate inner components of the connector; FIG. 7 is a diagrammatic top view of the connector; FIG. 8 is a diagrammatic top view of the connector with portions of the connector removed to illustrate inner components of the connector; FIG. 9 is a diagrammatic bottom view of the connector; FIG. 10 is a diagrammatic bottom view of the connector with the inner components of the connector illustrated; FIG. 11 is a diagrammatic rear view of the connector; FIG. 12 is a diagrammatic front view of the connector; FIG. 13 is a diagrammatic side view of the connector; FIG. 14 is a diagrammatic side view of a lower portion of the connector; FIG. 15 is a diagrammatic side view of the connector similar to that of FIG. 13, but from the opposite side of the connector; FIG. 16 is a diagrammatic side view of the lower portion of the connector showing the intravascular device positioned proximate to the lower portion of the connector; FIG. 17 is a close up diagrammatic side perspective view of a part of the lower portion of the connector; FIG. 18 is a close up diagrammatic side perspective view of an alignment feature of the part of the lower portion of the connector shown in FIG. 17; FIG. 19 is a close up diagrammatic side perspective view of the part of the lower portion of the connector with an intravascular device positioned within the lower portion; FIG. 20 is a close up diagrammatic side perspective view of the alignment feature of the part of the lower portion with an intravascular device positioned within the lower portion; FIG. 21 is a side view of the connector in an open position; FIG. 22 is a top view of the connector in the open position; and FIG. 23 is a side view of the connector in a closed position; and FIG. 24 is a top view of the connector in a closed position.

In some instances, the connectors of the present application incorporate one or more features of the connectors described in U.S. Patent Application No. 61/665,706, titled "SIDE-LOADING CONNECTORS FOR USE WITH INTRAVASCULAR DEVICES AND ASSOCIATED SYSTEMS AND METHODS," filed Jun. 28, 2012, which is hereby incorporated by reference in its entirety. In that regard, connector 104 is configured to interface with the connection portion 114 of the intravascular device 102 to facilitate communication between the intravascular device 102 and a separate component, such as a processing system. In particular, the connector 104 is configured to facilitate communication between one or more electronic components of the intravascular device 102 that are electrically coupled to the connection portion 114 and a separate component, such as a processing system associated with the one or more electronic components.

As shown in FIG. 5, the connector 104 includes an upper component 202 and a lower component 204. In the illustrated embodiment, the upper component 202 is movable with respect to the lower component 204. In particular, the upper and lower components 202 and 204 are slidable with respect to one another to facilitate insertion of an intravascular device into the connector 104 and subsequent engagement of the connector with the received intravascular device that results in one or more electrical connections between the intravascular device and the connector. In the illustrated embodiment, the upper component 202 includes an upper surface 206 with a gripping feature 208. In that regard, the gripping feature 208 is generally representative of any type of structure (e.g., projection(s), recess(es), combinations thereof, etc.), texture (e.g., roughened, knurled, patterned, combinations thereof, etc.) and/or combinations thereof configured to provide an interface to assist a user in translating the upper component 202 relative to the lower component 204. In the illustrated embodiment, the gripping feature 208 is a concave surface sized and shaped for interfacing with a user's thumb, as shown in FIGS. 5 and 13 for example. In that regard, the gripping feature 208 extends across a width of the upper component 202 in a direction that is transverse to the longitudinal axis of the upper component 202, as shown in FIGS. 5 and 7 for example.

As discussed below, the upper component 202 is configured to translate with respect to the lower component 204 along (or parallel to) the longitudinal axis of the upper component between open and closed positions such that the connector 104 is configured to receive the connection portion of an intravascular device, such as connection portion 114 of intravascular device 102, in a direction that is transverse to the longitudinal axis of the intravascular device. In that regard, the gripping feature 208 extends parallel to the longitudinal axis of the intravascular device when the intravascular device is received within and engaged with the connector 104. In some embodiments, the lower component 204 includes one or more gripping features similar to gripping feature 208 of upper component 202. In that regard, the lower component 204 may have the same, fewer, or more gripping features than the upper component 202, in the same or a different arrangement, and/or with the same or different structural profiles. In the illustrated embodiment, a lower surface 210 of the lower component 204 includes a gripping feature 212. In the illustrated embodiment, the gripping feature 212 is a concave surface sized and shaped for interfacing with a user's finger (such as the user's index/pointer finger), as shown in FIG. 13 for example. In that regard, the gripping feature 212 extends across a width of the lower component 204 in a direction that is transverse to the longitudinal axis of the lower component 204, such that the gripping feature 212 extends parallel to gripping feature 208 of the upper component 202. To that end, the arrangement of the gripping features 208 and 212 of the illustrated embodiment are particularly well-suited to allow a user to operate the connector 104 using one hand. In that regard, a user can advance and retract the upper component 202 relative to the lower component 204 with the user's thumb while maintaining the position of the lower component 204 relative to the user's finger to move the connector 104 between open and closed positions.

To guide the movement of the upper component 202 with respect to the lower component 204, in some embodiments the upper and/or lower component 202, 204 includes projections that are received within corresponding slots or openings of the lower and/or upper component 204, 202, respectively. In that regard, the slots or openings generally extend along the length of the component(s) in a direction parallel to the longitudinal axis of the component. The projections extend from the component(s) in a manner such that when the upper and lower components 202, 204 are assembled together the projections are received within the openings of the other component. In that regard, the projections are sized and shaped to be slidably received within the openings such that the projections can translate along the length of the openings when the upper component 202 is translated relative to the lower component 204. In some instances, the opposing ends of the openings 212 serve as stops to limit travel of the upper component 202 relative to the lower component 204. In that regard, the projection(s) will contact a first end of the opening when the upper component 202 is in the fully opened position and will contact a second end of the opening opposite the first end when the upper component is in the fully closed position. In some embodiments, the connector 104 includes a spring detent to lightly lock the mechanism in the closed position. In that regard, the spring detent biases the upper component 202 of the connector 104 toward the closed position through at least part of the sliding motion between the upper and lower components.

As shown in FIGS. 6, 8, 10, 22, and 23, the upper component 202 includes electrical contacts 214, 216, 218, 220, and 222. In that regard, the electrical contacts 214, 216, 218, 220, and 222 are configured to engage corresponding electrical contacts of an intravascular device, such as conductive portions 132, 134, and 136 of connection portion 114 of the intravascular device 102. For example, in the illustrated embodiment electrical contact 214 is configured to be electrically coupled to conductive portion 132, electrical contacts 216 and 218 are configured to be electrically coupled to conductive portion 134, and electrical contacts 220 and 222 are configured to be electrically coupled to conductive portion 136. It is understood, however, that any arrangement of electrical connection between the connector 104 and an intravascular device may be utilized. In that regard, the connector 104 may include any number of electrical contacts (e.g., 1, 2, 3, 4, 5, 6, 7, 8, or more electrical contacts), may include a single contact for each of one or more conductive portions of the intravascular device, may include multiple contacts for each of one or more conductive portions of the intravascular device, and/or combinations thereof. Further, in the illustrated embodiment the electrical contacts 214, 216, 218, 220, and 222 are split, open-comb electrical contacts. In that regard, each of the electrical contacts 214, 216, 218, 220, and 222 is configured to receive a conductive portion of an intravascular device therein such that some of the teeth of the open-comb electrical contact will be positioned above the conductive portion and others of the teeth of the open-comb electrical contact will be positioned below the conductive portion. This arrangement provides a secure and reliable electrical connection between the electrical contact of the connector 104 and the corresponding conductive portion of the intravascular device.

Further, as discussed below with respect to FIGS. 22 and 23, the open-comb electrical contacts are particularly well-suited to facilitate proper electrical connection between the connector 104 and an intravascular device positioned within the lower component 204 when the upper component 202 is translated relative to the lower component 204 from the open position towards the closed position. Further still, the open-comb configuration allows for the intravascular device to be rotated with respect to the connector while maintaining a proper connection. Thus, the open-comb configuration allows a user (e.g., surgeon) to keep the connector 104 connected to the intravascular device while the intravascular device is moved or advanced through the vasculature with little resistance to rotational movement of the intravascular device. In other words, the intravascular device can be moved through the vasculature, undergoing various twists and turns, without the connector 104 needing to move with the rotations of the intravascular device. Also, the open-comb configuration helps ensure good electrical contact due to the multiple fingers for each of the contacts. In addition, the open end of the open-comb configuration provides a good guide for ensuring that the intravascular device is correctly positioned when the upper component is closed onto the intravascular. While various advantages of the open-comb configuration have been described, it is understood that any appropriately sized electrical contacts can be utilized, including a single contact or a plurality of contacts.

As noted above, the connector 104 is configured to interface with a connection portion of an intravascular device to facilitate communication between the intravascular device and a separate component. In particular, the connector 104 is configured to facilitate communication between one or more electronic components of the intravascular device (that are electrically coupled to the connection portion) and a separate component, such as a processing system associated with the one or more electronic components. To that end, the connector 104 includes a communication cable 224 that is configured to carry signals between the connector 104 and the separate component. In particular, the cable 224 is configured to carry electrical signals and includes one or more electrical conductors extending along its length to facilitate such electrical communication. However, the type of communication cable utilized is dependent on the type of electronic, optical, and/or electro-optical components that are incorporated into the intravascular device. In that regard, the communication cable may include one or more of an electrical conductor, an optical fiber, and/or combinations thereof. In some instances, the cable is configured to be plugged into an interface of a processing system. In that regard, the interface is a patient interface module (PIM) in some instances.

As best shown in FIGS. 6 and 10, the cable 224 has a set of conductors 226. In the illustrated embodiment, the set of conductors 226 consists of five conductors such that each of the conductors is electrically coupled to a corresponding one of the electrical contacts 214, 216, 218, 220, and 222, In some instances, the electrical conductors 226 of the cable are soldered to the electrical contacts 214, 216, 218, 220, and 222 of the upper connection piece. However, generally any type of electrical connection may be used to electrically couple the conductors 226 of the cable 224 to the electrical contacts 214, 216, 218, 220, and 222 including, without limitation soldering, crimping, and/or insulation displacement connector (IDC). In the illustrated embodiment, the conductors 226 of the cable 224 are coupled to the electrical contacts 214, 216, 218, 220, and 222 by IDC.

As best seen in FIG. 11, a back portion of the upper component 202 includes an opening 228 extending therethrough to facilitate passage of the cable 224 therethrough. In particular, the opening 228 is configured to allow the cable 224 to extend through the upper component 202 from the coupling of the electrical conductors 226 of the cable to the electrical contacts 214, 216, 218, 220, and 222. The opening 228 is generally aligned with a larger opening 230 (See, e.g., FIG. 6) of the lower component 204. In that regard, the cable 224 extends through opening 230 in some embodiments. The arrangement of the openings 228 and 230 allows the upper component 202 to translate with respect to the lower component 204 without damaging the electrical couplings between the electrical conductors 226 of the cable 224 and the electrical contacts 214, 216, 218, 220, and 222 of the upper component and without creating unwanted kinking/bending of the cable. While in the illustrated embodiment, the electrical contacts 214, 216, 218, 220, and 222 are fixedly secured to the upper component 202, in other embodiments, the electrical contacts are fixedly secured to the lower component 204 and the lower component includes necessary recesses, openings, and/or passages to facilitate connection of the communication cable to the contacts and passing of the cable out of the connector.

As best shown in FIGS. 14, 16, 17, and 19, the lower component 204 includes a recess 232 that is sized and shaped to receive an intravascular device. In particular, the recess 232 is sized and shaped to receive a connection portion of the intravascular device. In the illustrated embodiment, the width of the recess 232 tapers from wider to narrower as the recess extends into the lower component 204. In that regard, the recess 232 includes a surface 234 and an opposing surface 236 that generally define the recess 232. The recess 232 is configured to maintain the connection portion of the intravascular device in position within the connector 104. In particular, the surface 236 is configured to maintain the intravascular device within the recess 232 as the upper component 202 is advanced relative to the lower component 204 and into engagement with the intravascular device. Accordingly, in some embodiments the surface 236 extends generally perpendicular to the longitudinal axis of the lower component to prevent the intravascular device from sliding up surface 236 and out of the recess 232 as the electrical contacts of the upper component 202 are advanced into electrical engagement with the intravascular device. In some particular embodiments, the surface 236 extends at an angle between about 60 degrees and about 120 degrees relative to the longitudinal axis of the lower component 204. In other embodiments, the surface 236 extends at an angle outside of this range (either smaller or larger). In the illustrated embodiment, the surface 236 extends at an angle of about 85 degrees relative to the longitudinal axis of the lower component, while the surface 234 extends at an angle of about 135 degrees relative to the longitudinal axis of the lower component (See, e.g., FIGS. 14 and 16).

In some embodiments, such as the illustrated embodiment, the recess 232 has discontinuities as it extends across the width of the lower component. In particular, as shown in FIGS. 17 and 19, the lower component 204 includes a plurality of supports 238, 240, 242, 244, 246, and 248 that collectively define the recess 232. In that regard, in the illustrated embodiment each of the supports 238, 240, 242, 244, 246, and 248 includes surface portions similar to surfaces 234 and 236 discussed above. In that regard, the supports 238 and 248 are outer supports that define the outer boundaries of the recess relative to lower component 204, while supports 240, 242, 244, and 246 are positioned between supports 238 and 248. In some embodiments, such as the illustrated embodiment, the supports 240, 242, 244, and 246 include tapered surfaces similar to surfaces 234 and 236 discussed above. However, in other embodiments the supports 240, 242, 244, and 246 comprise only the bottom portion of the recess 232 that is sized and shaped to receive the intravascular device. It is understood that, in other embodiments, the arrangement of the recess 232 as defined by outer portions 238, 248 is similar to that defined by supports 242, 244, and 246 and/or vice versa.

To help ensure that the connection portion of the intravascular device is properly aligned with the electrical contacts of the connector 104, the upper and/or lower component(s) 202, 204 may include one or more visual markers (active and/or passive) and/or be at least partially formed of a clear or translucent material. In that regard, one or more visual markers as described in U.S. Patent Application Publication No. 2014/0005573, titled "SIDE-LOADING CONNECTORS FOR USE WITH INTRAVASCULAR DEVICES AND ASSOCIATED SYSTEMS AND METHODS" and filed on the same day as the present application, are utilized in some instances.

Further, in the illustrated embodiment, the lower component 204 includes structure 250 configured to facilitate proper alignment of the intravascular device 102 with the connector 104. In that regard, as shown in FIGS. 18 and 19, for example, the structure 250 defines a recess or opening 252 that is generally aligned with recess or opening 232 extending across the lower component 204. In that regard, opposing outer portions 254 and 256 of support 248 taper into side surfaces 258 and 260 that define recess 252. Surfaces 258 and 260 are bounded by bottom surface 262. In the illustrated embodiment, the bottom surface 262 is concave. In some instances, the curvature of the bottom surface is sized and shaped to receive section 118 of the intravascular device 102. As shown, surfaces 258 and 260 extend parallel to one another and perpendicular to the longitudinal axis of the lower component 204 in the illustrated embodiment. However, in other embodiments, one or both of the surfaces 258, 260 extend at an oblique angle with respect to the longitudinal axis of the lower component 204.

As shown in FIG. 19, the recess 252 has a width 264 between the surfaces 258 and 260. As shown in FIGS. 15 and 18, for example, the width 264 of recess 252 is less than the width of the recess 232. In that regard, in some embodiments the width 264 of recess 252 is sized such that the section 118 of the intravascular device 102 can be received within the recess 252, but connection portion 114 and section 120 cannot be received within the recess 252. Accordingly, in some instances the width 264 of recess 252 is between about 0.0254 mm (0.001") and about 0.254 mm (0.01") greater than the diameter 124 of section 118, with some particular embodiments between about 0.0254 mm (0.001") and about 0.0508 mm (0.002") greater than the diameter 124 of section 118. The inability of the connection portion 114 and section 120 to be received within recess 252 can be utilized to align the intravascular device 102 with the connector 104. In that regard, the structure 250 also includes a surface 266 positioned adjacent the recess 252. The surface 266 is recessed into an outer surface 267 of the lower component 204. In that regard, cutout surface 268 extends between surface 266 and the outer surface 267. In some instances, the cutout 268 is sized and shaped such that the resulting surface 266 is configured to engage with a distal portion of section 120 of the intravascular device 102.

For example, in some implementations the structure 250 is utilized to align the intravascular device 102 with the connector 104 as follows. The user positions the intravascular device 102 within the lower component 204 such that section 118 is received within recess 252, the connection portion 114 is positioned at least partially within recess 232, and section 120 is positioned outside of the lower component adjacent outer surface 267 and recessed surface 266. While maintaining section 118 within the recess 232, the intravascular device 102 is advanced or translated such that the connection portion 114 is moved away from structure 250 while a distal surface of section 120 is brought into contact with surface 266, as shown in FIGS. 20 and 21. The spacing of the supports 238, 240, 242, 244, 246, and 248 of the lower component 204 and the corresponding spacing defined for the electrical contacts of the connection portion 114 to be engaged by the electrical contacts of the connector 104 are configured to be properly aligned with the connection portion 114 of the intravascular device 102 when the distal portion of the section 120 is in contact with an outer surface of the connector 104, such as surface 266 or surface 267. In that regard, it is understood that in some embodiments the lower component 204 does not include a recessed surface 266. In such embodiments, section 120 contacts the outer surface 267 to facilitate proper alignment of the intravascular device 102 relative to the connector 104. The simplicity of loading arrangement allows a user to place the proximal end of the intravascular device with section 118 past the connector feature 250. With the intravascular device angled slightly so that the proximal portion of the intravascular device is in contact with the opening of the slot section 118 will automatically drop into the slot. The intravascular device can then be pulled with slight tension and laid into the recess 232.

Alignment of the intravascular device 102 with respect to the connector 104 also facilitates use of an optional feature of the connector 104. In that regard, in some embodiments the connector 104 includes one or more wiping elements. For example, as shown in FIGS. 6, 8, 10, 13, and 22, the connector 104 includes wiping element 270 and 272. In that regard, the wiping elements 270, 272 are configured to remove liquid on the surface of the intravascular device 102 that can cause bridging between adjacent conductors. For example, in the illustrated embodiment, the wiping elements 270 and 272 are positioned such that when the upper component 202 is translated relative to the lower component 204 to engage a properly aligned intravascular device 102, wiping element 270 will remove liquid between conductive portions 132 and 134 and wiping element 272 will remove liquid between conductive portions 134, and 136. Accordingly, in some such instances the wiping elements 270, 272 are configured to engage insulating portions 140, 142, respectively. As best shown in FIGS. 13 and 22, the wiping elements 270, 272 of the illustrated embodiment each comprise two opposed pieces (upper and lower) such that the intravascular device 102 passes between the two pieces when the upper component 202 is moved to engage the intravascular device as discussed below with respect to FIGS. 22 and 23. Further, in the illustrated embodiment, each of the upper and lower pieces has a generally semi-cylindrical profile. However, it is understood that any structural arrangement of wiping element may be utilized, including a single element, multiple elements, geometrical, and/or non-geometrical profiles. Further, it is understood that the wiping elements can be formed of any suitable material, including without limitation sponge, polyurethane, silicone, polyethylene, EPDM, and/or vinyl.

Referring more specifically to FIGS. 22 and 23, shown therein is a transition of the connector 104 from the open positioned to the closed position. In that regard, the connector 104 is shown in the open position in FIG. 22 and the closed position in FIG. 23. As shown in FIG. 22, the connector 104 is configured to receive the intravascular device 102 in a side-loading fashion. More specifically, the recesses 232 and 252 in the lower component 204 are revealed when the upper component 202 is retracted to the open position such that the intravascular device 102 can be seated within the recesses by moving the intravascular device 102 in a direction transverse to its longitudinal axis.

To load the intravascular device within the connector 104, the connector 104 may be moved relative to the intravascular device 102, the intravascular device 102 may be moved relative to the connector 104, and/or combinations thereof. In some instances, with the intravascular device 102 positioned within the recesses 232 and 252 of the lower component 204, the intravascular device 102 is moved to engage section 120 with recessed surface 266 to properly align the intravascular device relative to the lower component while in the open position. In other instances, the intravascular device 102 is not moved to engage section 120 with the recessed surface 266 until after transitioning the upper component 202 to the closed position.

In that regard, with the intravascular device 102 positioned within the lower component 204, the upper component 202 is translated with respect to the lower component 204, as indicated by arrow 274 in FIG. 22, to the closed position illustrated in FIG. 23. In the closed position, the intravascular device 102 is held between the upper and lower components 202 and 204 such that the connector 104 is in electrical communication with the connection portion 114 of the intravascular device. In particular, as the upper component 202 is advanced towards the closed position the split teeth of the open-comb electrical contacts 214, 216, 218, 220, and 222 and the wiping elements 270, 272 engage the connection portion 114 of the intravascular device 102. In some instances, the bottom of the recess 232 is positioned relative to the electrical contacts 214, 216, 218, 220, and 222 such that the intravascular device will be aligned with the electrical contacts 214, 216, 218, 220, and 222 in the vertical direction when the intravascular device is seated within the recess. Accordingly, with the intravascular device 102 seated in the recess such that the conductive portions 132, 134, and 136 of the connection portion 114 are aligned horizontally (e.g., by using visual markers, engaging section 120 with surface 266, or otherwise) and vertically with respect to the electrical contacts of the connector 104, advancement of the upper component 202 to the closed position electrically couples the connector 104 to the intravascular device 102. Also, in the transition from the open position to the closed position, the wiping elements 270, 272 remove fluid from between the conductive portions 132, 134, and 136 to help prevent any bridging between the conductive portions. To disconnect and remove the intravascular device 102 from the connector 104, the upper component 202 is translated with respect to the lower component 204, as indicated by arrow 276 in FIG. 23, back to the open position of FIG. 22.

Referring now to FIGS. 24-30, shown therein are aspects of a connector 300 according to another embodiment of the present disclosure. In that regard, connector 300 includes many features similar to those described above with respect to connector 104. Accordingly, the following description will focus on features of connector 300 that are different than those of connector 104. However, it is understood that the various features of both connectors 104 and 300 may be combined in any of a variety of manners consistent with the present disclosure. In that regard, unless otherwise noted, it should be presumed that any feature of connector 104 may be implemented within connector 300 and vice versa.

Figure 25:
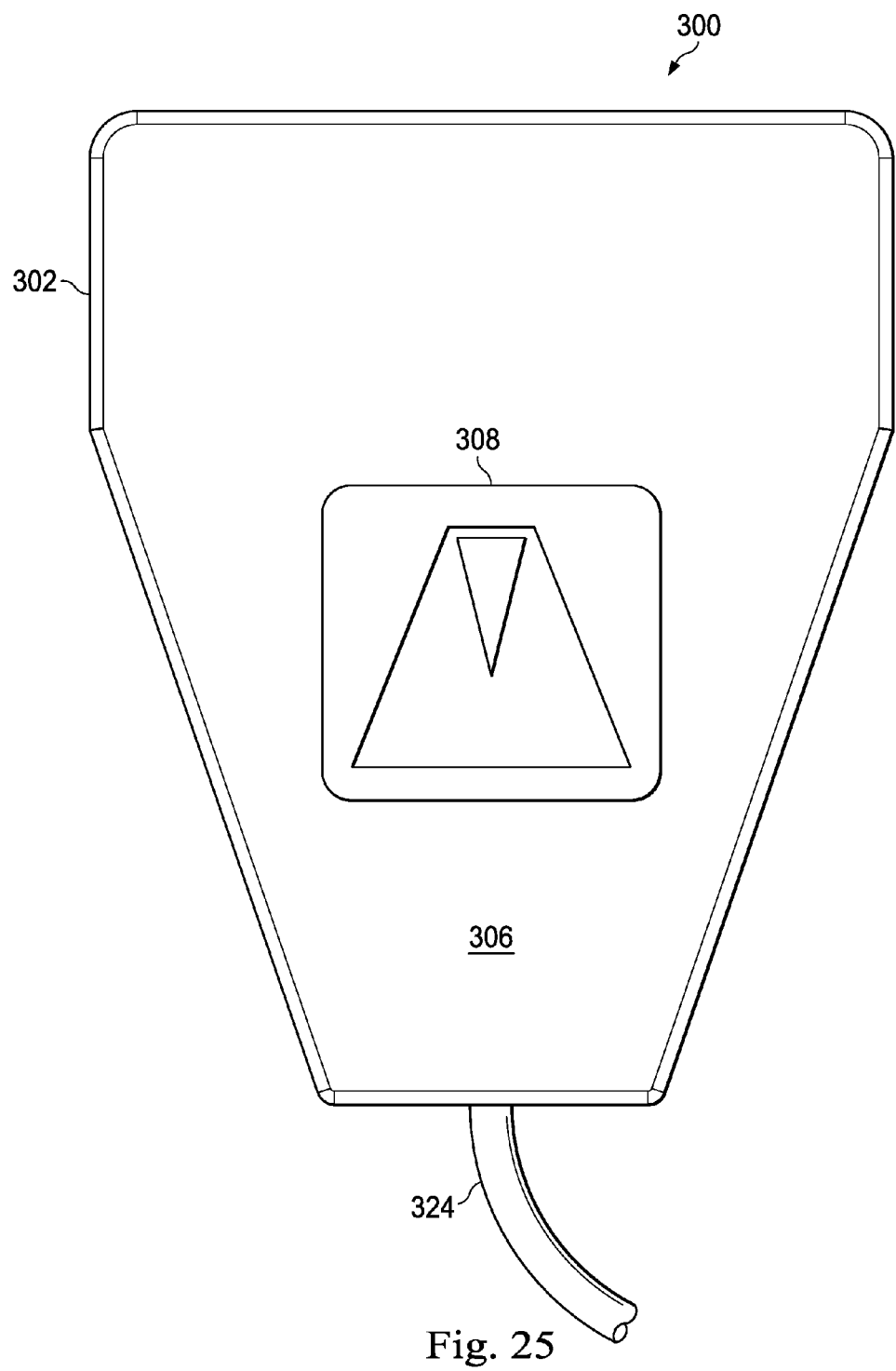
FIG. 25 is a diagrammatic top view of the connector of FIG. 24.
Figure 26:
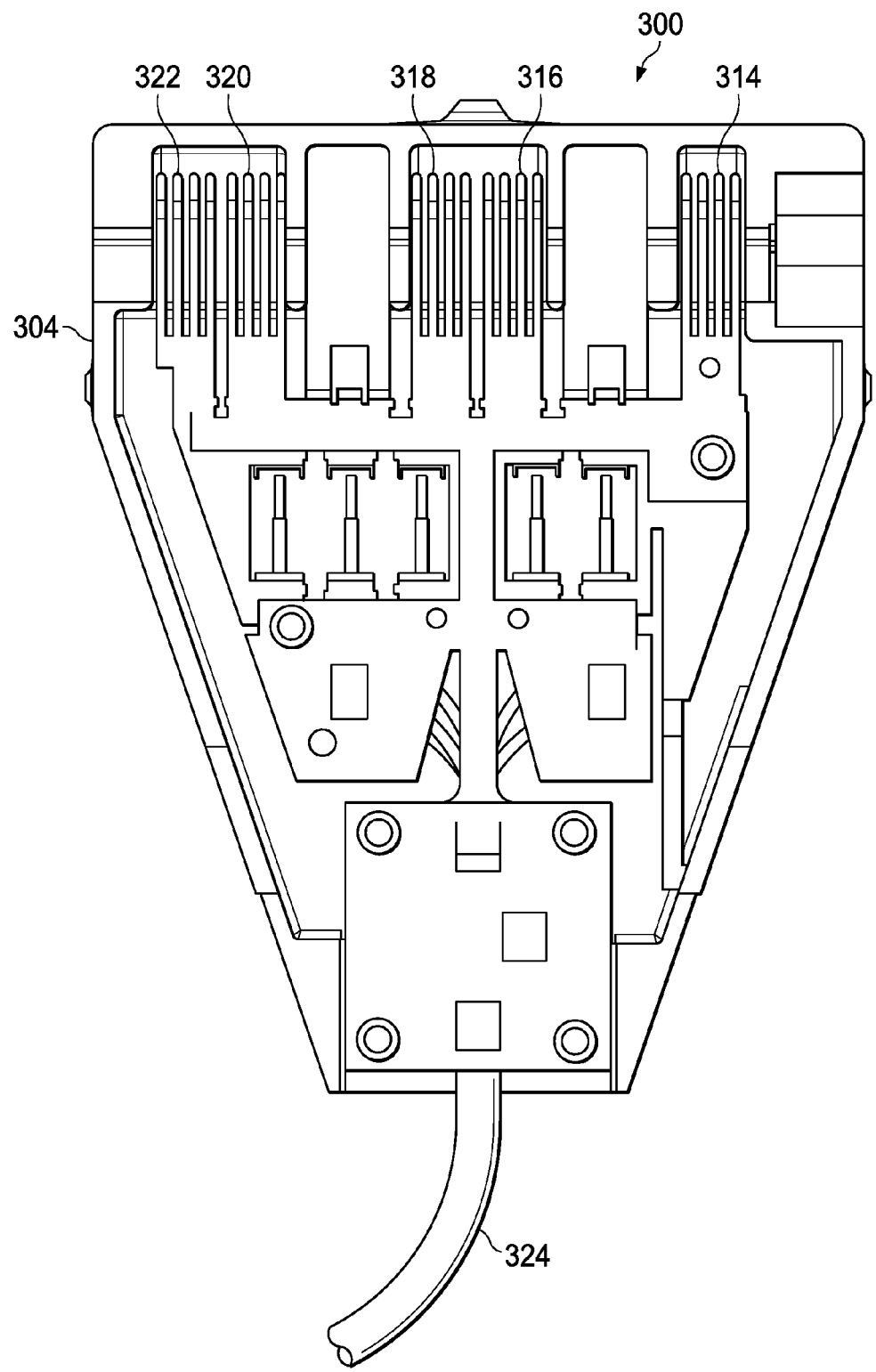
FIG. 26 is a diagrammatic top view of the connector similar to that of FIG. 25, but with portions of the connector removed to illustrate inner components of the connector.
Figure 27:
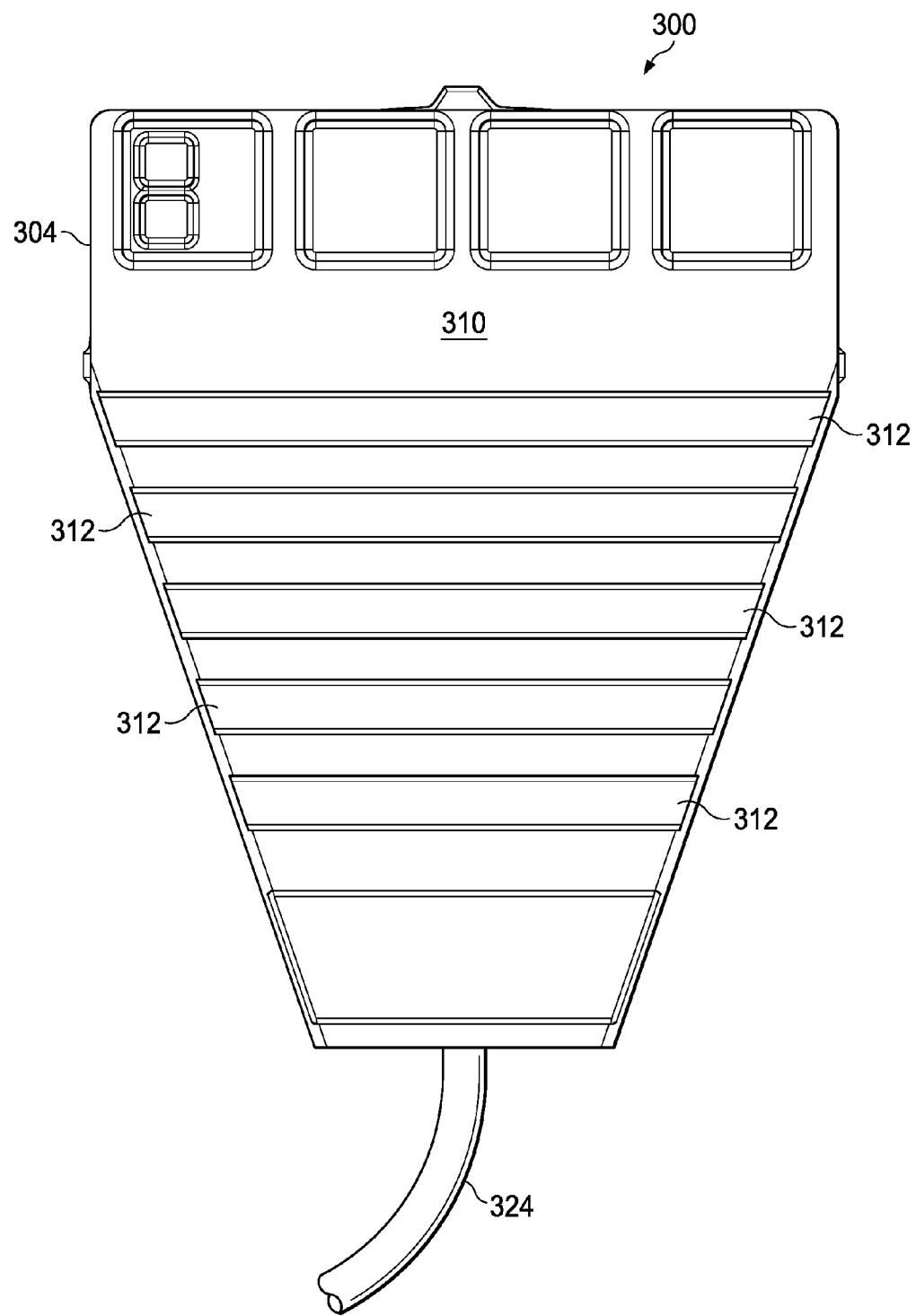
FIG. 27 is a diagrammatic bottom view of the connector of FIGS. 24-26.
Figure 28:
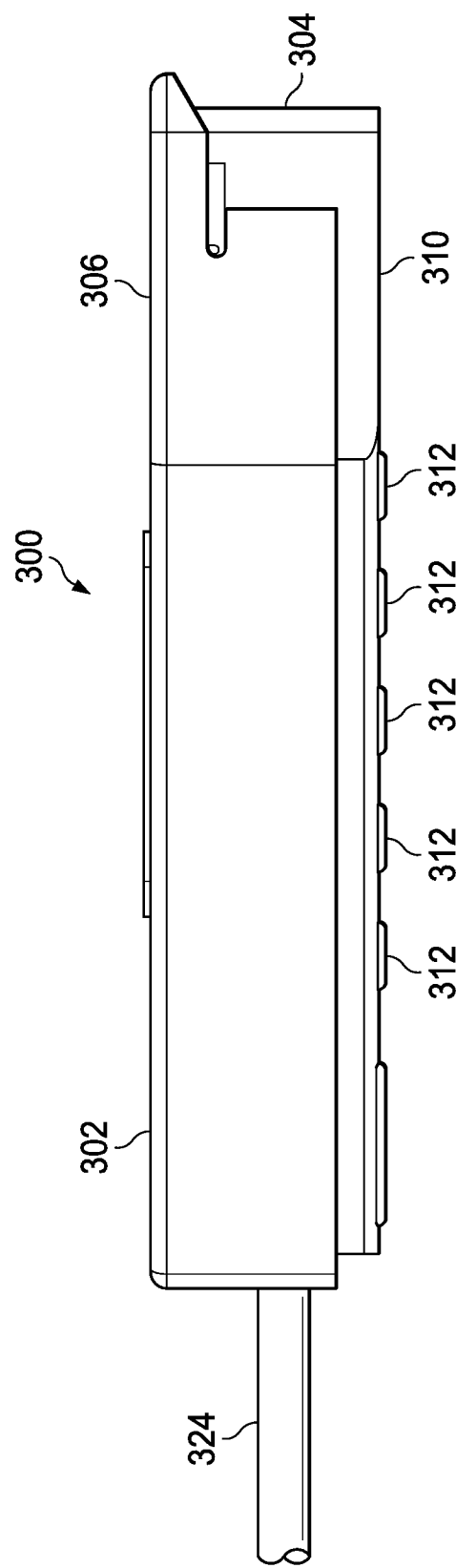
FIG. 28 is a diagrammatic side view of the connector of FIGS. 24-27.

As shown in FIG. 25, the connector 300 includes an upper component 302 and a lower component 304. In the illustrated embodiment, the upper component 302 is movable with respect to the lower component 304. In particular, the upper and lower components 302 and 304 are slidable with respect to one another to facilitate insertion of an intravascular device into the connector 300 and subsequent engagement of the connector with the received intravascular device that results in one or more electrical connections between the intravascular device and the connector. In the illustrated embodiment, the upper component 302 includes an upper surface 306 with a gripping feature 308. In that regard, the gripping feature 308 is generally representative of any type of structure (e.g., projection(s), recess(es), combinations thereof, etc.), texture (e.g., roughened, knurled, patterned, combinations thereof, etc.) and/or combinations thereof configured to provide an interface to assist a user in translating the upper component 302 relative to the lower component 304. In the illustrated embodiment, the gripping feature 308 is a raised surface portion. In some embodiments, the lower component 304 includes one or more gripping features similar to gripping feature 308 of upper component 302. In that regard, the lower component 304 may have the same, fewer, or more gripping features than the upper component 302, in the same or a different arrangement, and/or with the same or different structural profiles. In the illustrated embodiment, the lower surface 310 of the lower component 304 includes a plurality of projections or ridges 312 as gripping features.

The upper component 302 includes electrical contacts 314, 316, 318, 320, and 322. In that regard, the electrical contacts 314, 316, 318, 320, and 322 are configured to engage corresponding electrical contacts of an intravascular device, such as conductive portions 132, 134, and 136 of connection portion 114 of the intravascular device 102. For example, in the illustrated embodiment electrical contact 314 is configured to be electrically coupled to conductive portion 132, electrical contacts 316 and 318 are configured to be electrically coupled to conductive portion 134, and electrical contacts 320 and 322 are configured to be electrically coupled to conductive portion 136. It is understood, however, that any arrangement of electrical connection between the connector 300 and an intravascular device may be utilized. In that regard, the connector 300 may include any number of electrical contacts (e.g., 1, 2, 3, 4, 5, 6, 7, 8, or more electrical contacts), may include a single contact for each of one or more conductive portions of the intravascular device, may include multiple contacts for each of one or more conductive portions of the intravascular device, and/or combinations thereof. Further, in the illustrated embodiment the electrical contacts 314, 316, 318, 320, and 322 are split, open-comb electrical contacts. In that regard, each of the electrical contacts 314, 316, 318, 320, and 322 is configured to receive a conductive portion of an intravascular device therein such that some of the teeth of the open-comb electrical contact will be positioned above the conductive portion and others of the teeth of the open-comb electrical contact will be positioned below the conductive portion. This arrangement provides a secure and reliable electrical connection between the electrical contact of the connector 300 and the corresponding conductive portion of the intravascular device.

Further, the open-comb electrical contacts are particularly well-suited to facilitate proper electrical connection between the connector 300 and an intravascular device positioned within the lower component 304 when the upper component 302 is translated relative to the lower component 304 from the open position towards the closed position. Further still, the open-comb configuration allows for the intravascular device to be rotated with respect to the connector while maintaining a proper connection. Thus, the open-comb configuration allows a user (e.g., surgeon) to keep the connector 300 connected to the intravascular device while the intravascular device is moved or advanced through the vasculature with little resistance to rotational movement of the intravascular device. In other words, the intravascular device can be moved through the vasculature, undergoing various twists and turns, without the connector 300 needing to move with the rotations of the intravascular device. Also, the open-comb configuration helps ensure good electrical contact due to the multiple fingers for each of the contacts. In addition, the open end of the open-comb configuration provides a good guide for ensuring that the intravascular device is correctly positioned when the upper component is closed onto the intravascular. While various advantages of the open-comb configuration have been described, it is understood that any appropriately sized electrical contacts can be utilized, including a single contact or a plurality of contacts.

As noted above, the connector 300 is configured to interface with a connection portion of an intravascular device to facilitate communication between the intravascular device and a separate component. In particular, the connector 300 is configured to facilitate communication between one or more electronic components of the intravascular device (that are electrically coupled to the connection portion) and a separate component, such as a processing system associated with the one or more electronic components. To that end, the connector 300 includes a communication cable 324 that is configured to carry signals between the connector 300 and the separate component. In particular, the cable 324 is configured to carry electrical signals and includes one or more electrical conductors extending along its length to facilitate such electrical communication. However, the type of communication cable utilized is dependent on the type of electronic, optical, and/or electro-optical components that are incorporated into the intravascular device. In that regard, the communication cable may include one or more of an electrical conductor, an optical fiber, and/or combinations thereof. In some instances, the cable is configured to be plugged into an interface of a processing system. In that regard, the interface is a patient interface module (PIM) in some instances.

Figure 29:
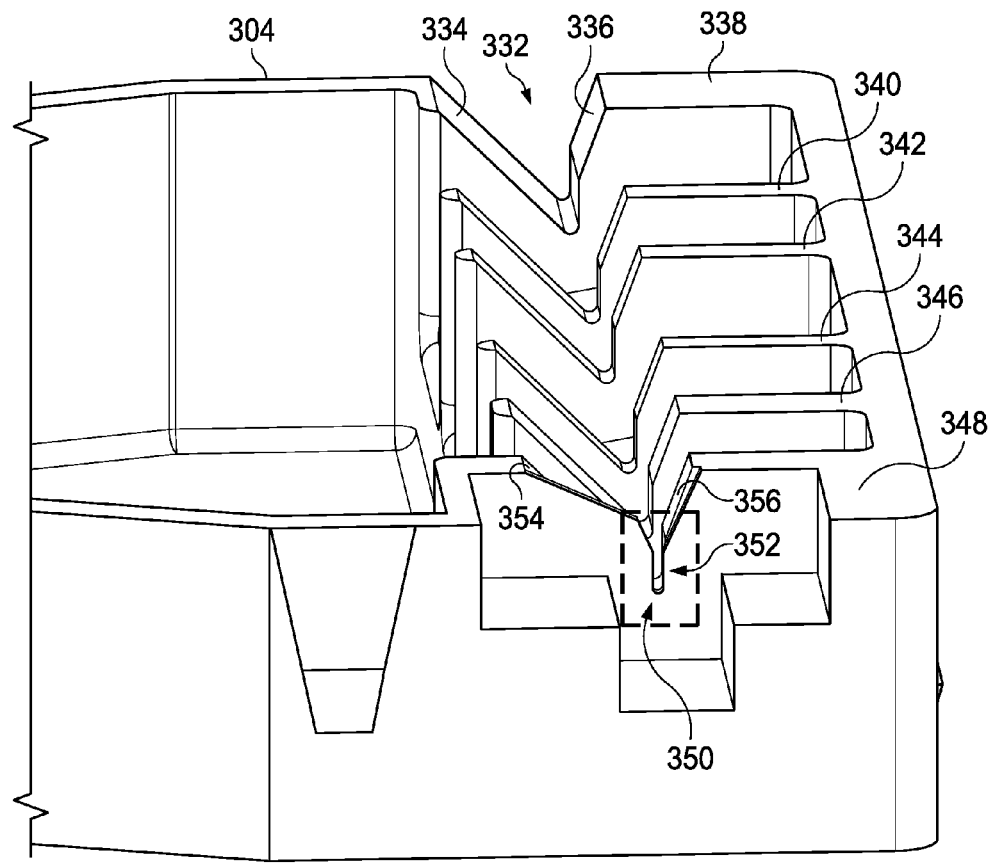
FIG. 29 is a close up diagrammatic side perspective view of a part of the lower portion of the connector of FIGS. 24-29.

As best shown in FIG. 29, the lower component 304 includes a recess 332 that is sized and shaped to receive an intravascular device. In particular, the recess 332 is sized and shaped to receive a connection portion of the intravascular device. In the illustrated embodiment, the width of the recess 332 tapers from wider to narrower as the recess extends into the lower component 304. In that regard, the recess 332 includes a surface 334 and an opposing surface 336 that generally define the recess 332. The recess 332 is configured to maintain the connection portion of the intravascular device in position within the connector 300. In particular, the surface 336 is configured to maintain the intravascular device within the recess 332 as the upper component 302 is advanced relative to the lower component 304 and into engagement with the intravascular device. Accordingly, in some embodiments the surface 336 extends generally perpendicular to the longitudinal axis of the lower component to prevent the intravascular device from sliding up surface 336 and out of the recess 332 as the electrical contacts of the upper component 302 are advanced into electrical engagement with the intravascular device. In some particular embodiments, the surface 336 extends at an angle between about 60 degrees and about 120 degrees relative to the longitudinal axis of the lower component 304. In other embodiments, the surface 336 extends at an angle outside of this range (either smaller or larger). As shown in FIG. 29, in the illustrated embodiment, a lower portion of the surface 336 extends at an angle of about 90 degrees relative to the longitudinal axis of the lower component, an upper portion of the surface 336 extends at an angle of about 70 degrees relative to the longitudinal axis of the lower component, and the surface 334 extends at an angle of about 135 degrees relative to the longitudinal axis of the lower component.

In some embodiments, such as the illustrated embodiment, the recess 332 has discontinuities as it extends across the width of the lower component. In particular, as shown in FIG. 29, the lower component 304 includes a plurality of supports 338, 340, 342, 344, 346, and 348 that collectively define the recess 332. In that regard, in the illustrated embodiment each of the supports 338, 340, 342, 344, 346, and 348 includes surface portions similar to surfaces 334 and 336 discussed above. In that regard, the supports 338 and 348 are outer supports that define the outer boundaries of the recess relative to lower component 304, while supports 340, 342, 344, and 346 are positioned between supports 338 and 348. In some embodiments, such as the illustrated embodiment, the supports 340, 342, 344, and 346 include tapered surfaces similar to surfaces 334 and 336 discussed above. However, in other embodiments the supports 340, 342, 344, and 346 comprise only the bottom portion of the recess 332 that is sized and shaped to receive the intravascular device. It is understood that, in other embodiments, the arrangement of the recess 332 as defined by outer portions 338, 348 is similar to that defined by supports 342, 344, and 346 and/or vice versa.

To help ensure that the connection portion of the intravascular device is properly aligned with the electrical contacts of the connector 300, the upper and/or lower component(s) 302, 304 may include one or more visual markers (active and/or passive) and/or be at least partially formed of a clear or translucent material. In that regard, one or more visual markers as described in U.S. Patent Application Publication No. 2014/0005573, titled "SIDE-LOADING CONNECTORS FOR USE WITH INTRAVASCULAR DEVICES AND ASSOCIATED SYSTEMS AND METHODS" and filed on the same day as the present application, are utilized in some instances.

Figure 30:
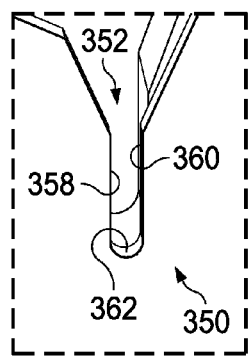
FIG. 30 is a close up diagrammatic side perspective view of an alignment feature of the part of the lower portion of the connector shown in FIG. 29.

Further, in the illustrated embodiment, the lower component 304 includes structure 350 configured to facilitate proper alignment of the intravascular device 102 with the connector 300. In that regard, as shown in FIGS. 29 and 30, the structure 350 defines a recess or opening 352 that is generally aligned with recess or opening 332 extending across the lower component 304. In that regard, opposing outer portions 354 and 356 of structure 350 taper into side surfaces 358 and 360 that define recess 352. Surfaces 358 and 360 are bounded by bottom surface 362. In the illustrated embodiment, the bottom surface 362 is concave. In some instances, the curvature of the bottom surface 362 is sized and shaped to receive section 118 of the intravascular device 102. As shown, surfaces 358 and 360 extend parallel to one another and perpendicular to the longitudinal axis of the lower component 304 in the illustrated embodiment. However, in other embodiments, one or both of the surfaces 358, 360 extend at an oblique angle with respect to the longitudinal axis of the lower component 304.

The recess 352 has a width between the surfaces 358 and 360 that is less than the width of the recess 232. In that regard, in some embodiments the width of recess 352 is sized such that the section 118 of the intravascular device 102 can be received within the recess 352, but connection portion 114 and section 120 cannot be received within the recess 352. Accordingly, in some instances the width of recess 352 is between about 0.0254 mm (0.001") and about 0.254 mm (0.01") greater than the diameter 124 of section 118, with some particular embodiments between about 0.0254 mm (0.001") and about 0.0508 mm (0.002") greater than the diameter 124 of section 118. The inability of the connection portion 114 and section 120 to be received within recess 352 can be utilized to align the intravascular device 102 with the connector 300. For example, in some implementations the structure 350 is utilized to align the intravascular device 102 with the connector 104 as follows. The user positions the intravascular device 102 within the lower component 304 such that section 118 is received within recess 352, the connection portion 114 is positioned at least partially within recess 332, and section 120 is positioned outside of the lower component structure 350. While maintaining section 118 within the recess 352, the intravascular device 102 is advanced or translated such that the connection portion 114 is moved away from structure 350 while a distal surface of section 120 is brought into contact with an outer surface of structure 350. The simplicity of loading arrangement allows a user to place the proximal end of the intravascular device with section 118 past the connector feature 350. With the intravascular device angled slightly so that the proximal portion of the intravascular device is in contact with the opening of the slot section 118 will automatically drop into the slot. The intravascular device can then be pulled with slight tension and laid into the recess 332.

Figure 31:
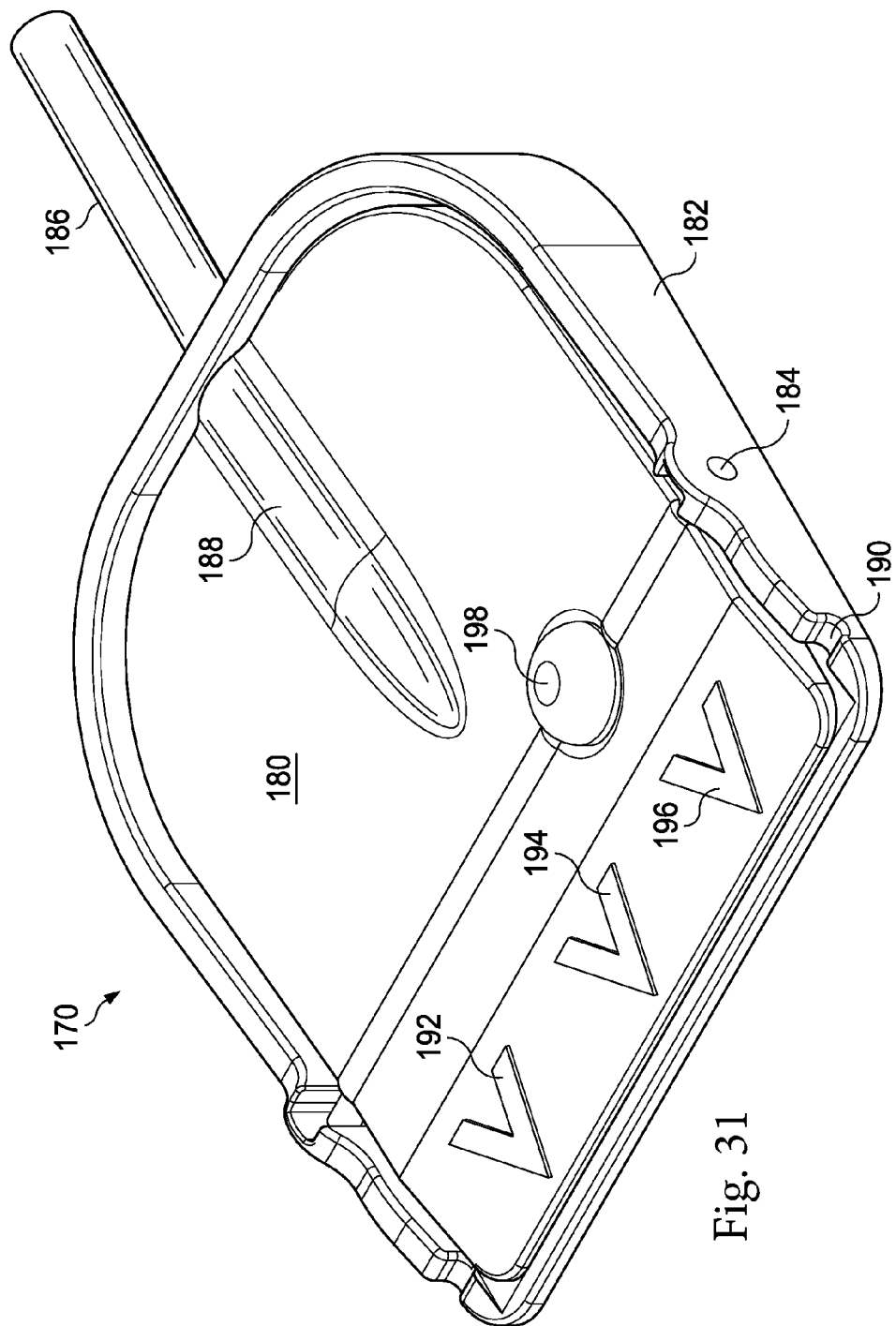
FIG. 31 is a diagrammatic perspective view of a connector of the intravascular system of FIG. 1 according to another embodiment of the present disclosure.
Figure 32:
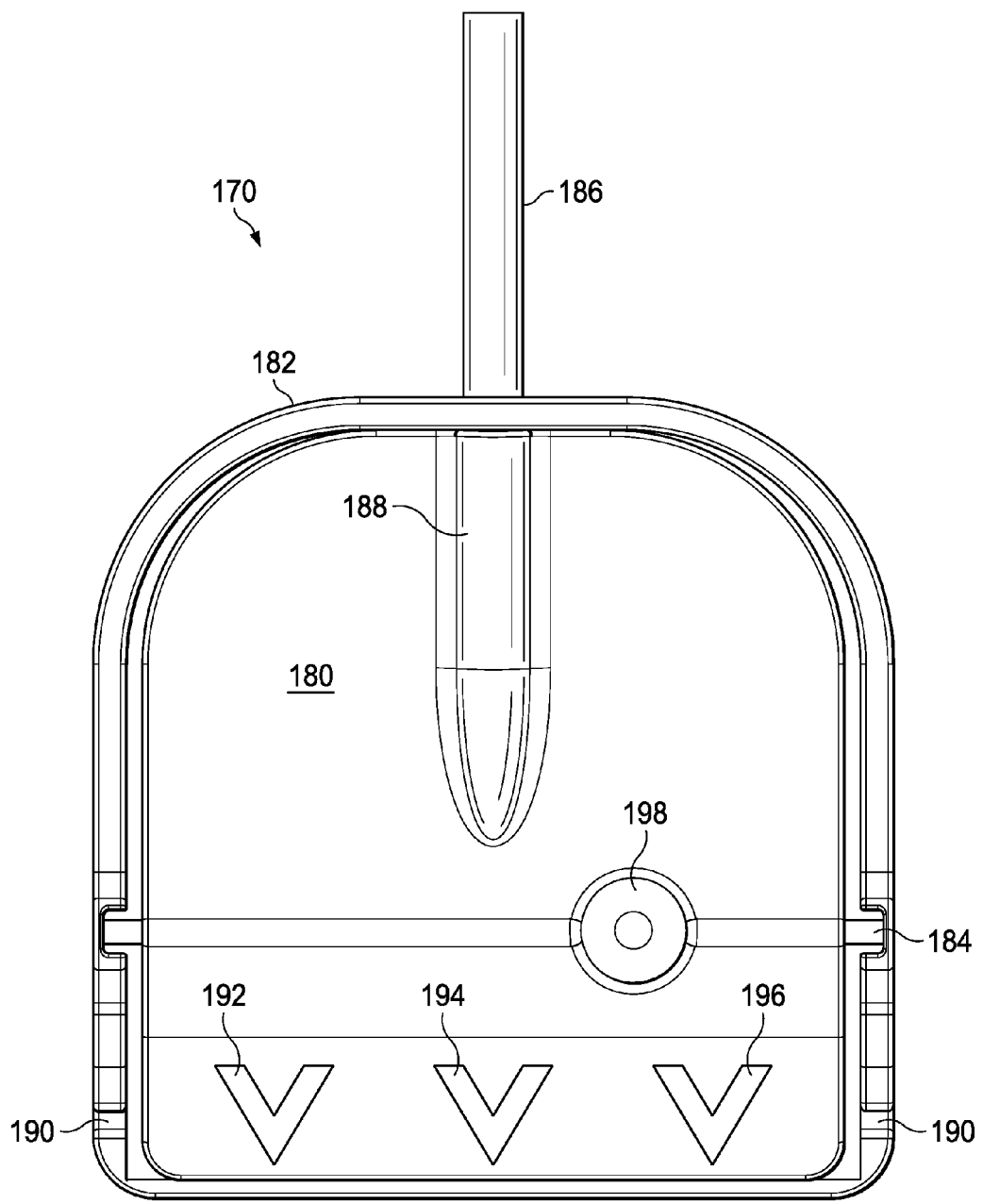
FIG. 32 is a diagrammatic top view of the connector of FIG. 31.

Referring now to FIGS. 31 and 32, shown therein is a connector 170 according to another embodiment of the present disclosure. In that regard, connector 170 includes some features similar to connector 104 described above. However, connector 170 includes an active element for indicating a connection state of the connector 170. Connector 170 is configured to interface with the connection portion 114 of the intravascular device 102 to facilitate communication between the intravascular device 102 and a separate component, such as a processing system. In particular, the connector 170 is configured to facilitate communication between one or more electronic components of the intravascular device 102 that are electrically coupled to the connection portion 114 and a separate component, such as a processing system associated with the one or more electronic components. As shown in FIG. 31, the connector 170 includes an upper connection piece 180 and a lower connection piece 182. In the illustrated embodiment, the upper connection piece 180 is movable with respect to the lower connection piece 182 about a pivot pin 184. In some instances, the pivot pin 184 is fixedly secured to the lower connection piece 182. Further, the pivot pin 184 extends through a portion of the upper connection piece 180 and/or engages a structural feature of the upper connection piece (e.g., recess(es), clamp(s), snap-fit element(s), projection(s), etc.) to ensure that the upper connection piece 180 pivots about the pivot pin 184.

In some embodiments, the upper connection piece 180 is biased towards either an open position (for receiving the connection portion 114 of the intravascular device 102) or closed position (for electrically coupling to the connection portion 114 of the intravascular device 102) by a bias element. For example, in some instances the bias element is configured to bias the connection piece 180 towards a closed position such that a user can release the connector 170 after insertion of the intravascular device and the bias element will maintain the connector 170 in electrical contact with the connection portion 114 of the intravascular device. In some instances, the bias element is a spring. In some particular instances, at least a portion of the spring is wrapped around the pivot pin 184. In that regard, the pivoting motion of the upper connection piece 180 relative to the lower connection piece 182, and the structural arrangements to facilitate such motion, operates in a manner to a clothes pin or a chip clip.

As noted above, the connector 170 is configured to interface with the connection portion 114 of the intravascular device 102 to facilitate communication between the intravascular device 102 and a separate component, and, in particular, the connector 104 is configured to facilitate communication between one or more electronic components of the intravascular device 102 (that are electrically coupled to the connection portion 114) and a separate component, such as a processing system associated with the one or more electronic components. To that end, the connector 170 includes a communication cable 186 extending therefrom. The communication cable 186 is configured to carry signals between the connector 170 and the separate component. In the illustrated embodiment, the cable 186 is configured to carry electrical signals and includes one or more electrical conductors extending along its length to facilitate such electrical communication. However, the type of communication cable utilized is dependent on the type of electronic, optical, and/or electro-optical components that are incorporated into the intravascular device 102. In that regard, the communication cable 186 may include one or more of an electrical conductor, an optical fiber, and/or combinations thereof. In some instances, the cable 186 is configured to be plugged into an interface of a processing system. In that regard, the interface is a patient interface module (PIM) in some instances.

As shown in FIG. 32, for example, the cable 186 extends through an opening on the back side of the lower connection piece 182. The upper connection piece 180 includes a projection or protrusion 188 in its upper surface that defines a corresponding recess or opening thereunder for receiving at least a portion of the cable 186. In that regard, in some instances one or more electrical conductors of the cable 186 are positioned within the recess or opening defined by the protrusion 188. Further, the one or more electrical conductors of the cable 186 are electrically coupled to one or more electrical contacts associated with the connector 170. In that regard, in some embodiments the electrical contacts are fixedly secured to the upper connection piece 180. In some such instances, the one or more electrical conductors of the cable 186 are soldered to the electrical contacts of the upper connection piece. However, in other embodiments, the electrical contacts are fixedly secured to the lower connection piece 182. In some instances, gold plated copper alloy contacts are utilized. However, it is understood that any suitable electrical contacts can be utilized by the connector 170.

In some instances, the cable 186 is replaced with a wireless connection (e.g., a wireless antenna). In that regard, it is understood that various communication pathways between the connector 170 and another component of the intravascular system may be utilized, including physical connections (including electrical, optical, and/or fluid connections), wireless connections, and/or combinations thereof.

As shown in FIGS. 31 and 32, the lower connection piece 182 includes a recess 190 that is sized and shaped to receive the intravascular device 102 therein. In particular, the recess 190 is sized and shaped to receive the connection portion 114 of the intravascular device 102. In that regard, the width of the recess 190 is typically sized to be slightly larger than the diameter of the connection portion 114 of the intravascular device 102. The recess 190 helps to maintain the connection portion 114 of the intravascular device 102 in position within the connector 170. To help ensure that the connection portion 114 of the intravascular device 102 is properly aligned with the electrical contacts of the connector 170, the upper connection piece 180 includes visual markers 192, 194, and 196 that provide an indication of the location of the electrical contacts and, therefore, where the electrical contacts or connectors of the connection portion 114 of the intravascular device 102 should be aligned. For example, similar to the visual markers 152, 154, and 156 of connector 104 shown in FIG. 11 of U.S. Patent Application No. 61/665,706, the visual markers 192, 194, and 196 are configured to be aligned with the conductive portions 122, 124, and 126, respectively, of connection portion 114 to facilitate connection of the connector 170 to the intravascular device 102.

In the illustrated embodiment, the visual markers 192, 194, and 196 are arrows. However, it is understood that any type of visual markers may be utilized including, without limitation, projections, recesses, colors, shapes, and/or combinations thereof. In that regard, in some embodiments the visual markers are color-coded to match correspondingly colored visual markers associated with the electrical contacts or connectors of the intravascular device 102. Further, in the illustrated embodiment the connector 170 includes an active element 198 to provide an indication of whether a proper connection between the connector 170 and the connection portion 114 of the intravascular device 102 has been achieved. The active element may provide a visual signal, an audible signal, and/or combinations thereof representing a connection between the connector 170 and the connection portion 114. In the illustrated embodiment, active element 198 is a light emitting diode (LED) that illuminates when a proper connection is achieved between the connector 170 and the connection portion 114. For example, in some instances the active element 198 is off when no connection or an improper connection and illuminates when a proper connection is made. In other instances, the active element 198 illuminates a first color (e.g., red) when no connection or an improper connection is made and illuminates a second, different color (e.g., green) when a proper connection is made. In yet other instances, the active element 198 illuminates a first color (e.g., red) when no connection or an improper connection is made, illuminates a second, different color (e.g., yellow) when a partial connection is made, and illuminates a third, different color (e.g., green) when a full proper connection is made. The active element 198 has been described as being applicable to the overall connection between the connector 170 and the connection portion 114. However, in other embodiments, a separate active element is provided for each connection between a conductor of the connector 170 and a conductor of the connection portion 114.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular system, comprising:
an intravascular device comprising:
a flexible elongate member comprising a proximal portion and a distal portion;
at least one physiologic sensing component disposed at the distal portion of the flexible elongate member;
at least one electrical contact disposed at the proximal portion of the flexible elongate member and electrically coupled to the at least one physiologic sensing component and; and
an engagement feature disposed at the proximal portion of the flexible elongate member; and
a connector configured to interface with the proximal portion of the intravascular device, the connector comprising a mating engagement feature and at least one electrical contact,
wherein the connector is movable between an open position and a closed position,
wherein in the open position the connector is configured to receive the proximal portion of the intravascular device in a direction transverse to a longitudinal axis of the intravascular device such that the engagement feature of the intravascular device engages the mating engagement feature of the connector, and
wherein the at least one electrical contact of the connector is configured to interface with the at least one electrical contact of the intravascular device.

2. The system of claim 1, wherein connector includes a visual indicator representative of electrical coupling between the connector and the intravascular device.

3. The system of claim 2, wherein the connector comprises a first connection piece and a second connection piece, wherein the visual indicator is disposed on the first connection piece.

4. The system of claim 2, wherein the visual indicator is a light.

5. The system of claim 4, wherein the light is configured to illuminate when a proper electrical coupling is achieved between the connector and the intravascular device.

6. The system of claim 4, wherein the light is configured to:
illuminate a first color when a proper electrical coupling is achieved between the at least one electrical contact of the connector and the at least one electrical contact of the connector; and
illuminate a second color when the proper electrical coupling between the at least one electrical contact of the connector and the at least one electrical contact of the connector is not achieved.

7. The system of claim 4, wherein the light is configured to:
illuminate a first color when complete electrical coupling is achieved between the at least one electrical contact of the connector and the at least one electrical contact of the connector;
illuminate a second color when partial electrical coupling between the at least one electrical contact of the connector and the at least one electrical contact of the connector is achieved; and
illuminate a third color when no connection and/or improper connection is achieved between the at least one electrical contact of the connector and the at least one electrical contact of the connector.

8. The system of claim 2, wherein the connector includes a plurality of visual indicators each associated with an individual connection between the at least one electrical contact of the connector and the at least one electrical contact of the connector.

9. The system of claim 1, wherein the connector includes an indicator configured to output an audible signal indicative of electrical coupling between the connector and the intravascular device.

* * * * *